(12) United States Patent
Hamelink et al.

(10) Patent No.: US 11,584,939 B2
(45) Date of Patent: Feb. 21, 2023

(54) TBRFV RESISTANT TOMATO PLANT

(71) Applicant: RIJK ZWAAN ZAADTEELT EN ZAADHANDEL B.V., De Lier (NL)

(72) Inventors: Roel Hamelink, De Lier (NL); Jonathan Kalisvaart, De Lier (NL); Hamed Rashidi, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/930,651

(22) Filed: May 13, 2020

(65) Prior Publication Data
US 2020/0399652 A1    Dec. 24, 2020

Related U.S. Application Data

(63) Continuation-in-part of application No. PCT/EP2018/084031, filed on Dec. 7, 2018, which is a continuation-in-part of application No. PCT/EP2017/082096, filed on Dec. 8, 2017.

(51) Int. Cl.
*C12N 15/82* (2006.01)
*A01H 5/08* (2018.01)

(52) U.S. Cl.
CPC .......... *C12N 15/8283* (2013.01); *A01H 5/08* (2013.01)

(58) Field of Classification Search
None
See application file for complete search history.

(56) References Cited

U.S. PATENT DOCUMENTS

2020/0077614 A1† 3/2020 Ashkenazi

FOREIGN PATENT DOCUMENTS

| EP | 17305644.1 | † | 6/2017 |
| WO | 2013/064641 A1 | | 5/2013 |
| WO | 2018/219941 A1 | | 12/2018 |

OTHER PUBLICATIONS

Sequence Accession EU557673, Jun. 4, 2008 (Year: 2008), attached sequence alignment at the end of the Office Action.*
Ainong Shi, et al., Molecular Markers for Tm-2 Alleles of Tomato Mosaic Virus Resistance in Tomato, American Journal of Plant Sciences (2011) 2:180-189.
Ann-Maree Cataazariti, et al., The tomato /-3 gene: a novel gene for resistance to Fusarium wilt disease, New Phytologist (2015) 207:106-118.
P. Kadirvel, et al., Mapping of QTLs in tomato line FLA456 associated with resistance to a virus causing tomato yellow leaf curl disease, Euphytica (2013) 190:297-308.
Neta Luria, et al., A New Israeli Tobamovirus Isolate Infects Tomato Plants Harboring Tm-22 Resistance Genes, PLOS ONE I DOI:10.1371/journal.pone.0170429 Jan. 20, 2017.
N. Salem, et al., A new tobamovirus infecting tomato crops in Jordan, Arch Virol (2016) 161:503-506.
Wojciech Szczechura, et al., Tomato Molecular Markers. Vegetable Crops Research Bulletin (2011) vol. 74:5-23.
EMBL Accession No. CP023767 *Solanum lycopersicum* (tomato), Nov. 20, 2017.
EMBL Accession No. CP023768 *Solanum lycopersicum* (tomato), Nov. 20, 2017.
ISR and Written Opinion dated Mar. 13, 2019 in International Application PCT/EP2018/084031.

\* cited by examiner
† cited by third party

*Primary Examiner* — Elizabeth F McElwain
(74) *Attorney, Agent, or Firm* — Duane Morris LLP; Thomas J. Kowalski; Deborah L. Lu

(57) ABSTRACT

The invention relates to a *Solanum lycopersicum* plant that is resistant to TBRFV, which plant comprises a QTL on chromosome 11 between SEQ ID NO: 1 and 53. The presence of the QTL on chromosome 11 is identified by use of at least one of the markers selected from the group comprising SEQ ID NOS: 4 to 52. The QTL is as comprised in the genome of a *Solanum lycopersicum* plant representative seed of which was deposited with the NCIMB under deposit number NCIMB 42882, NCIMB 42885, NCIMB 42887, or NCIMB 42890.

19 Claims, 7 Drawing Sheets

Specification includes a Sequence Listing.

Figure 1 – Marker sequences SEQ ID Nos. 1-53. The SNP is underscored and bold.

SEQ ID No. 1

TTTATGGGACGTTGAGCATCTCATGAACTTACGGAGATTTCTAGTTGAGTTGTGTGATCAAGTGGTAGATTTAA
CGTTGTGTACTATCTCTAAAAGCTTGGTCTTACCAAGAGGAATTTATCGTCTTCCTACACTTGAAGTCGAGAATT
TGGAACTGTCTTATAGTGATATTACAACCGCGACATATTCATTTTACTATGA

SEQ ID No. 2

ACACATTAATAAGTTTCAAGTACCGATAAAGGCAAATTTTTATCATGGGTTAGCAAAGCAAGATGAGTAAGGT
ATCTGTAGAATTAGATATACTCAACCATGTCTAAAAGGTGTGTCACTTTCAGATGCCTACATTTACCGAAAAAA
GATAATCTTGCTTTTATGGGCTTTAACCAAATACACAAGAATGGGATGCAACAG

SEQ ID No. 3

AGAAACAACCCCTCTACCTAACACAAGGTATGTGTAAGGTCTAAGTAGACTCTACTATACTAGATATGTTATTG
TTGTTGAGAAATGTAATATGAGGGTCGGAAACATCCACTCTACCTAACACAAGGTATGTGTAAGGTCTACATA
GACTATTATACTGAATATGTTATTGTTGTTGAGAAATGTAATCTGAGGGTCGGA

SEQ ID No. 4

GAGAGAGCGAATCTGCAAAGCTGATTTCCGATGCTACTGCGGCTGCTGGAATGGGTTTGATTGAGCTGAGGA
GGATTGAAGCTTCTAGAGAAGTTGCTGGGACTTTGGCTAAGACTCCTAATGTTGCTTACTTGCCTAAGCAAGG
GAATATGCTTCTTGGACTCGGCCGTTGAGTAGGTAATCAATTGAGCAAAATGCTAG

SEQ ID No. 5

TTGTAGTTAACTAATTAAATTTAGAATMTYCATCCTACAACGCAAGTTAAAAACACTCGTAAATCCGGACACAT
GTTGTAGGATTAGGGGTAGATGTTTTTGAGGCTATTAATAGTGTAGAGATAAAAGTTTTGGAGTGTTTTCAATA
CATCTGTCTYGTTAGAAAAAGGTCGAGGCCCACGTTAACCGGCCATTGTCACC

SEQ ID No. 6

GTTTCATTGTGTTAAGAATTGTGCCTGGGAAAATGGGTCTCTGATGGAATGGCAAAAGAAAGTTTATGTGTTA
CTGAAGCTTTTCGGTTATTGAAGAAGAGGAAGAAAAAAACTATATGGGGAGTTCACAGCAGTCCGGTAGCTTT
GGGGACCCTCAACAAATCTCCTCTGATAATGTTAATGGTCTTTGCTTGGCTATTT

SEQ ID No. 7

TGAGAAGAAAAGAAGCAGAGTTCAATGTAATGTCACTACAACTTTCTTTATTYTGATCTGAAAGATTGTCAGCT
CCACAAACAGTACCAGACACAGACACGACTGCCACATTGATTAGGAAGGACACAAAYAACGCGAAACCGCTCT
CTATCAAGAAGAATTTACATGCATCCTACAAAATYCAACATTAATTAATTTTTC

SEQ ID No. 8

AGCTACTATCARTTTTCCAAGAACTTTGCTTCTATTGCAACTCATTTGACTAGTCTGACTCAGAATGAAGTGCCT
TTAGTTGTAGTCCGACCAGTGAAAAAAGAGCTTTCAAAAGCGCAAGACATTTTTGACTATGATCCMAACATTA
GGGGTGGAAGGTAATGACTACATTGTATRTTGTGATGCTTCACATTTGGGTTT

SEQ ID No. 9

CACTCGTGACATGCCTTCACTTCATCCCCGTTACCCCTCAACTTATAAACCCCATATTCTATCTATCAAGACTTAT
ACCCGCTTCAGTACCACATCTTTCTGGGTCAACATTACAACATGTCACCACCCCCATCCTCAATGACAATACACA
TGACCATATTTCTAAAACACAACAACACCGAGACTTTTAGTCTCCACCTA

Figure 1 Continued

SEQ ID No. 10

ATTGGTGGTAATAGAGATTCTGTGACTGGTGGTGGTGGTGATTCTGTGAYTGGTGGAGGAGGTGATTYTGTGA
CTGGTGGTGGTGGAGATGTAGGCTAATTTGATTTTGGGGAAGATGGAGAAGATGTAGACGGTTTGTTTGTGG
TTGATTTTCTTCCCCCTGAGCAGGTACTGTATCAATGAMAGGGTTCTCTTCCCCCT

SEQ ID No. 11

TTAAGAGTTTCAATATCCTTTGTGGTATCGTCAAGAAAATCTTGCAGAGCAGAAAGATTTTTTTGGAGAGATTC
GACATGTTGTTGTGTACAACTTCGACGAACGAAAGATTGGTTAGGTTTGAAGAGTTGTTCTAATGTATACATAA
GTGAAGAAAGAGCAGCATAAGCCATTTCTCTTAACAACAATTATTGCTAAAGA

SEQ ID No. 12

CATCAGATTCCTGCAAAATATAATTACACCTCACTTAAGAAGTACTTGCCTTTAGGTATGAAGCCACCTGCAATA
TATTTCAGAAAAAACAGTGAAAAGTGACGAGTCAGTAAAAAAAATGAAACAAGAGTGTAACCAATAAAATTA
AAAAAATTCTCCTTCTCACCCATGCGAAAAGTGCTGAAAAACCAACACCAACTC

SEQ ID No. 13

AGTCCTTATCTATTATTATATGGTGAACAAGTCAATAAAAATACTCGTAATTGAAATAGTTATCGATAATTGTTC
ACTTCCCTCTTATGGAATTCGAGTTTACAATTATGATGTGTTGTTGAATAGTGTAAGAATTGATGCATCATCACT
TAAATATATTCTGTTAGAAATATTATTGAATTCATTGTACAATCCATTTGT

SEQ ID No. 14

CTCAATCGAAGGTACTTTGGAAGTATCATCCCTGAGATGTGCCAAGAAAGCTACACAACCCTTACTCATCATCC
TGTTAGCACGAAGAAAAGAGATAATACGAACTGGAGTGGAAATTTAGTCACCCTCCCACACTAGCGGATCTGT
CCCAGGCTTGGCCAATATTACAGTTTTAGCATTACAATCTAAGATTGCAAAATT

SEQ ID No. 15

TCAAATCATCAAGAAACGTCCATGACGTCAGGAAACTAGTTCAAGAGGTGTTGATGTGCGTTAGCCTATTTGA
CTAGGTTTTAGGAGTCAGAATTTGATGGAATTCGGTAGTAAGGTGTCTAATACGTATTCGAGTTGTTTTATAGT
CAAAAATTCTGGGTACGACTCTCCAAGGACCAACCAAAGGGCCCTTGAGGAGGA

SEQ ID No. 16

AATTGGCCTTTCCTCTTTCTAGTTGAAAAAAAAAACAAAACAAAGAGGTATATGCACCAATTAACATCAATTGT
GAATTCACCAGTGACGATATCTACTTCAAAAGATGTTTGTCTTCTACTGAATACAGGATATGAATTAAATTTTCT
AGCTCCAAGACACCAATTTAGCATAACTATAKTTATAATACTACAAAAAAAA

SEQ ID No. 17

AACAAACAATACGAAACTCTATGCCTAAAAATACACATATCAACGAAACTGACATAACATATCTCCCATTGATTT
TAAAATTGTTGAAAATGCTTACAATTGTTAATTCCACTAGATTTGAGAGTAGACAAACAATTAATGAAACTCAA
TTCCTAAAATACACATGAAAATTACCATAACTATATAAATAAGGTGATTTTT

SEQ ID No. 18

GCATTAAAATCCATTGCATTACTAATGCATAGAACTCCATGGTATTAGTAATATGCTAATGCATGCATTAGAATC
CATTGCACTACTAATGCATAGAACTTCATGGTATTAATAATACTCTTCAATACACAATAAATTGTATTACTAATA
CAAGCATTAGTTATGCATACGTTAGAAAAGTGTACTAAACAAGGTACTAGT

Figure 1 Continued

SEQ ID No. 19

GCATGCATTTAGAAGAGAAATGCTGTTTTATAAACTTCAACTAAAATAACCTGCAATTTCTTTAAACATTGAAGA
AAGGCCATGAGCAACATTGCTAGGGATGGGTTGGGCACCCTCATCACCAAGGACCAATTTAGCATCTGCATTC
ATCACCGCAACATCAAACATGGGACGTAATCCCACGTAGTGTTGCATGGCACT

SEQ ID No. 20

AAATTTCCTCTTTTCTACCTCAAATTCGTACAGCAAGAGCATGCTTGGCATGAGACCAAACACACGCGGAGATT
CCGGAGGTAACCATGGTATGGTCATGT

SEQ ID No. 21

CACATATTAATGAAAGGAATATCCCAATTCAAATTGATGTCACCATAGGACCATCAACTAGTGGCATAGCTAAT
GAGTCAAAAGCACGCCTAAAGCGTGGCAGGCCATTTGGATCAAAACCCTAGAAAATGAAAATCAAAAGATCA
AAATGACACTATGAAAAAACCTCACATAGAAAGTCAAGACGTGAGTAATTCTGAT

SEQ ID No. 22

TCAATCAATAGGAGCGACGGGCGGTGTGTACAAAGGGTAGGGACGTAGTCAATGCGAGCTGATGACTCGTGC
TTACTAGGAATTCCTTGTTGAAAACCAACAAATGCAATGATATATCCCTATCACGATGAAATTTCAAAGATTACC
CGGGCCTATTGGCCAAGGCTATAAACTCGTTGAATAATCAGTGTAGCGCGCGTG

SEQ ID No. 23

TTCAATAAGCTTAATACTTAATGGATCTAAGAATATATATTATTCATTTGATCAATTTGAGATAAACTATAAACC
ATACAATAATAATCTATACATAAATAAAGAGTCTATAACAATCTATACATGAATTCATTAATATCAAAGCATGAT
CACACAACCCATATTTAAGTCAAATTGAGAGATTTGAGAAGGTCAAGGGTT

SEQ ID No. 24

GGAGGTGTCTGGCCCTGATCAGATAACCCGCTAAGATAAGCCAGAACCTGATTGATCATCTCTGGGGTAGGTT
GGGGTGGCATTTCCTCATTCTACACTTTTTCATTCTCCTCATCCTCCCCTTCTCTTACTACTTCCTCAGTTGGTGGA
GGAGTCACCGCCCTAGTACCAGATGGGCCAGGCGTTCGTCCTCTTCCTCTA

SEQ ID No. 25

GGACCTTCCACATAAGTTTCAACAAAAACGAACACGTAAAACATGTAAAGGTACACCAAGACACACATGCATG
TCTCAAGTCTAACCTTCAAACGTCATCAGACATTCTTGGACATTTGACCTCCAAATGATTTCAAATTAATCATAC
ATTCTTAAAACACTTAATTAACAGGTGAACAAGATTATTACACACATGTGAGG

SEQ ID No. 26

GTTGAAGGTTCCACATAAAGGACCTTATTAGAAACATTCAAGGTCTCATGTCATTCGTACATACAAGACTAAGA
GACTTTAGCATCCTAATTCAATACATATGATATTCATATTCATCCATGTATCAAGTAAGGGACACAAGTCTACCA
CACAAGATACACAAATACTTCACTTTACCCCATATAACATATAATTCTAGAA

SEQ ID No. 27

AACCAACATTAYACAATTCATATCAAGATAACAACCTRGGGTTAAGTGTTAAAGGTCATTTTCTACAAACTAGA
CTGATTTATCAACAAATAACATAATTAAGTTAAAGTACATGTTAAACTATTCATGACATCCATAATAAATCATAA
ATAAAGTAATTCACAAGCCCAATTTCAAGATTTGAAAAGACTCACTTGAATT

Figure 1 Continued

SEQ ID No. 28

CGCTAAAGGAACCGAATAAAATGGGAGATCTTCGGAGAGAATGGATTTTGTTGAAGTTGGGGAAGTGTGGAA
TCTTGTGATGGAATGAGAGTGAATGGGT<u>T</u>AGGTAGTGGGGGGAAAAAAGAGGAAATAGGGAGGGAAACGG
TTAAGGGGGTTATGTAAAGAGGTGGGTAACTGAAGAGTTTAAAAACTTTTCATATGTAG

SEQ ID No. 29

AACTCTCATACTCGTTCATTCAATGTCCTGATTTTTGTTGGCCTGTATCGTATCATGATGCATACGCAGGTAACG
AGGATCGACATCCAATGCATCATTG<u>G</u>TTCAGTTGAGCACTCCAGAGTCGGTTGGTGCGCCTCTTTGCTTTTTGG
AGGATCCATTTTATTTCTTTCTAGTTTAGTTTATTAGGATCTGTCCCAACAC

SEQ ID No. 30

GATTTAATGAACAAGATATTCAAACAATATTTGGACTTGTTTGTCATTGTCTTTATTTATAATATCCCGATTTATT
CTCAAAGTGAGAAAGAGCATCCGA<u>A</u>CCATATGAGAGTTTCTATGCAAACTCTCAAAGATCGACAATTATTCACT
AAGTTCAACAAATGTTAATTCTTGTTACAGTCGGTTGCATTCCTTGGTCAT

SEQ ID No. 31

AGAAACAACTAAATTAAGTTGTTGCCATTTGACAATATAAGCCAACAATAATTTCGTTGTTGCTAAAACGTTGCT
GCGAATTGTACATTTTCTTGTAGTG<u>T</u>GTGACAGAAATTGTTGCTTGTCTTAGCAAGGTTTACGATGATCATCTCA
GCAGGTTAGTTTTACATAGCATCCACTAATTTGYTGGAATTTTCTGAAAAA

SEQ ID No. 32

TTTTAAATTGGTTCCATTTTTTACTATAAAATTCTTTTTGAATTTGTTTTCGTGCCAGGGATCCTGGACTAAAATC
AATGAGTCGATTAAACATAATTAA<u>G</u>CATCATTGAGATCAGTTGATTTATCAACACTGAAGTCCATTTCTGACTG
AGTTGGATCCATATCTGACAACTTATCAGTTGCTTGAACAATATTTGTTCT

SEQ ID No. 33

GATGGATTCGTAAATTCAATACGTGATTCCAAGATAAGCATGTTAATTTTAGGAAAAAAATCTTCAATTTTCTTT
TACCATTTTTCTTTCTTTGGGTGGA<u>A</u>AGATTCCTCGTCTTCAAATGGAAATACTAAACGAAATGTTACTTTGACA
AAAGAACGTTCCTTCTCTTTTGGAGGAATGACTTCATTATGATAGTGGACT

SEQ ID No. 34

TGTTACTCTTATATGAAGTTGTTTACGTTAATGAACATGTTATTGGTCTTACTTCTTTATGAGGTGATAAGTACTT
ATGTTACAAGTTATATGAAGCAAA<u>C</u>CTTTACTTATGGTCTCCTATCTTATTTATTTTGTTGTGTAACACCTAAATA
TGAACTATGGTGAACTTGAGCTTCGTAAGTGTTTCTTTAATTATATGAA

SEQ ID No. 35

TGGTAATGGAAATAATAGTTACAATCACGGAAAGTCACATATTTACTGTGAGTTCTACCATTACAAAGGTCACA
CTAAAGAGACTTACAAGCTTTATGAC<u>C</u>ATCCTAAGAAGAAAGATGGAGCATCGATCTATCCCTCATGTTAAGGT
TGTTTCTATTGGGGAATCAACTCACTAAGGCTAGAGTTATGACTAGGTCCTAT

Figure 1 Continued

SEQ ID No. 36

TTTGCACATGGCCAAGATATACTAGAAACGCATTATAGTTTTGTTAAATGTTTTATCCTAAGTTTTGGCTRTAAG
GTAAACTATTACTCAAGCATGGAGCCTGTCTTAATAATATACATATTAATGTATAGCAGTTCTAACATAGGTTTC
AGGCTGCCCCTTTCTTCAACAATTAACGGGGACTTACAATACCACATGCTC

SEQ ID No. 37

TTATCCTTCCCTTGGATTTTGAGAAAGCCGCAAATTCTTAATTTCTCCCATTCGAGTTGACTCGTAGAAAAGGCG
AAAAGGTCCCGAAGTTTAAAGAATCAAAGAAGATTGAAGAAATTGAATGGTTTGGGCAAAAAGTCCAAAAAT
TTTATTTTGGAAAAATGTTGTATTTTATTTGGGCCTAAGCCCTTTTGTATTGTT

SEQ ID No. 38

CCAGATCGTGCTTAGATTGATTTTTGAACTCCATTTCAGCAGATTCAGTGGTGAGTCCTCATCCTCTAAGGACG
ATATTCATGAGTTTCTTTTTAGTGTTTGGTTCTTTTGTTTCAGTTTTTGCTAGACTTTTTTGGGGCTTATGCCAAC
ATTTCTAGTCAGTTTAGAGGCTATTTTCAGACATAGTTAGTTTCAGCTTAG

SEQ ID No. 39

ACACCGATGCAACTTTGCTTTCATTTTGATATATGTCACACTAGAAACAGTGCTACATTTTAAATATTTAAATGT
AGTGGGAGTATTATATCTATGTAAATTTTTTTATGCTATTTTTTGGGTTTCATGGAAGTTTTTTTTCGATACTTTG
GCCAAGGACAGTCCCGTTTAACTATATAATTTTTTAAATTTTCTAGGATT

SEQ ID No. 40

GTCCCTCCAAGGCTTCGCTTGCTTAAATAATAGGGAAATATACATCTTTTTGGCTGATCGCTAAGTATACTTGGC
GATGCTTAGGTGTTTCTCTTCATATCTTTTCATCATTTTTTCACGTTTTGCGCCTAAGTGTCACTGCCAACACTAA
AACTTCAAATACTTGAAACTTAAGAGTTTTCATCAGACATTGAGATAGAA

SEQ ID No. 41

AACATTAAAATATGTGTATACGATGAATATATGATGTTTTCATGAGGTTTCCTTGATGAATTTTACTAGTTGATT
ATGAAGGTGATCATTGTGATTTAGGCCGTTAAAGGTGTGATTTAGGCTATTAATTCTATTGTCTTGTTTTAGTGT
TCTAGATTGATCTTTTTAATTCAATTGTCTTGAAATTAATTGATCGTAGTA

SEQ ID No. 42

GTGTCCAAGGCAAACCTACAACAAAATCCACATTGATGTCTTCCCACATCCAAGTAGGAACTTGGATTTCTTGG
AGTAAACCACCTGACTTTTGGTGTTCAGCTTTTACTTCTTGGCAATTTGGAGATTTTGCAACAAATTCCACTATA
TCCTTCTTCAAGCCTTCCCACCAAAACACTTCGCTAAGGTCATGGTTCATCT

Figure 1 Continued

SEQ ID No. 43

TCTCCTATGGCCTATACAGATATATGATGGTTAATGAAGGCTTAAAGACATTTTAAAAAGGGACTTTATCTTAG
CACCGAGCGAACTAAATATGAGAGGT<u>G</u>TTTTTTCCCAATGTGGGAAGGTAGGTTTGTAATGGTTCTTATGAGA
TGGAGATAACAGTGCAATGTTCATAAAGACGGTCTCTAGCATATATCCTAGTTA

SEQ ID No. 44

TCCATCTTTGAACATAGTAGTATTTTTTCTTTAGACTTCATGTTGTTGGGATATGTATGAAATAATGTTGTTCACA
TTCCCAATATTTCCCGCATCAACC<u>G</u>AAAAATTGTTAATTTTTACGAGCTCTTCTCACCTAGATTTCTCTATATTAA
TCGATTGGATGAATTTGCTGATATTAGAGTAAACCGATAACCTACATCC

SEQ ID No. 45

GTTTGATTAGTTGTTTGTTTATAATTTTCGTTTTGGGTTCTTCAAGTGTGAAGAACTTTAGTTTACCTACTGTTAT
TGTACGTTATTTGGCAGAGAAAAA<u>C</u>GTGAGTGAGAGTAATAGAGACGTGAGAGAGAGAGATGAGCATGGGA
GAGAAGAGTTTTCTTAGGCTTAGGAGTCTAGTTTAGGACTTAGTCAAATAAGTT

SEQ ID No. 46

ATCTGCAAACAAAAAGTGACAACATTAATAGGAGGATMCATTAGCCAAGTKTTGTGTGCTTTGGAAAATCGAC
ATTGACTAATGGTACAGAACATCAACC<u>A</u>WCCTAAACACATGTAACATGCCATGTGCGCATCTTGAAAACAACT
TTGACCAATGGAACGCAACATWAGAAAAGGCCGGTCCACTTTGTGCAAGAGGCAT

SEQ ID No. 47

GTTTAGGTTAGCGTGTAGTGGTATTTTTTAGGGTGTGGGGTTAAGGATTTGAAGTTAAATATCTATGGTGTAGT
GTTTAATTTTTTGGATTTTGTATTTT<u>T</u>GTCATGAGGTTTAGGGTATAGGGTATAGGTTAAAGTGTTATGATTAGG
GTTAGGGCTAAGGTTAGAGGTAGGGTTAWGATTTAGTGTTCGAGTTTAGGAT

SEQ ID No. 48

AATGTTGTCATGTTTGCTTTAAAAATTTATATATAAAAATATAAAAGTATTTTATACAAAATATATAGAAAAAAT
TGAGGAGAAAAAAACTTGATTTTTT<u>T</u>AAAAAAATTGGACCAATTGGTGAAAAAAAATTGGCTCTAAAAACTAA
ACTCTAAAATTTAAATAGTCATCCAAATATATTTATATTTTTAAAATCTAACA

SEQ ID No. 49

TAGAAGATGATGGACTTTCTGATGTATCTGAGCTGCTATTCTCACTTTGTCTATCTTTATTTGACCATAGTTTTGG
GAACATCTTTTTGGACCAATTATT<u>A</u>AAGATTGATAAACTTGGATAGTGGTAGATTTGGATCTCTAGCAACTTCA
GTATCGATTACCTTAGCCACCTTTACTCCGGAATCATCTGATGCAAACGGG

SEQ ID No. 50

ATATCATAACATTTAAGAGTACATAACATCATGATACTTTAACAATATAGACCAACACATATTCATAAGTGACAC
AATCAACATATAGTATCAACAATGT<u>T</u>CAAGTTTATCATATGCATGCCAGATAACATTACAATCATATTCATACAT
AAGAACATCCTCCTAAGACTCCCTTCAAGGCTAACTAGTGCGATGTTTTGT

Figure 1 Continued

SEQ ID No. 51

CTCTCACTTTGAATATTCAGTTTCCTCATTTCATCAATAGGAAGTGTTCCTTCCCCTATATTTCCCTGATAATTGCT
CAAATTAGCTCCAAACACACCACCATTTCTACTAGCTCCAAAAACAAACCCTTCATTACCAACATCCCCACTACC
CCTATCAACCCCAGAAGCAAAACCCACATTCCCAAATTTCCCAGGAACC

SEQ ID No. 52

GGTATTCACTATCCTGTATTAATATCTGTTGCACATGTTCCAGAACTTAACTATATAAGAGTTGAGGATGATGG
CTTAGAAATAGGTGCTGGAGTTAAGTTGTCACAGCTT

SEQ ID No. 53

TAAAGTAGCGTGTAACCATTGGTGATGCATGTAAAGGGAATTTTCTAAATACAATCATTTTTTCTTCAAAGTTAA
CCATTTGTAGCTTTAACTGTTCAATAGCCTTGCACATAAGGTGTATCCTTCTTGGCCCTCTGTTTAGACAAAGTA
CCATCAATAGGATGAGAGTTACAGAAAAAAGTAGCAGAAGTACTTCTCAGA

TBRFV RESISTANT TOMATO PLANT

RELATED APPLICATIONS AND INCORPORATION BY REFERENCE

This application is a continuation-in-part application of international patent application Serial No. PCT/EP2018/084031 filed 7 Dec. 2018, which published as PCT Publication No. WO 2019/110821 on 13 Jun. 2019, which claims benefit of international patent application Serial No. PCT/EP2017/082096 filed 8 Dec. 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named 00460SL.txt and is 19.5 kb in size.

FIELD OF THE INVENTION

The present invention relates to a tomato (*Solanum lycopersicum*) plant which is resistant to Tomato brown rugose fruit virus (TBRFV). The invention further relates to a method for producing such *Solanum lycopersicum* plant and methods for identification and selection of such a plant. The invention also relates to progeny, seed and fruit of the Tomato brown rugose fruit virus resistant *Solanum lycopersicum* plant, to propagation material suitable for producing the *Solanum lycopersicum* plant, and to a food product comprising such tomato fruit or part thereof. The invention further relates to a cell or a tissue culture that results from or can be regenerated into a Tomato brown rugose fruit virus resistant *Solanum lycopersicum* plant. The invention also relates to a marker for identification of Tomato brown rugose fruit virus resistant *Solanum lycopersicum* plants, and to use of said marker.

BACKGROUND OF THE INVENTION

One of the problems that is encountered when growing a tomato crop (*Solanum lycopersicum*) is the occurrence of various viruses. Resistance against many known viruses has been identified, which resistances are incorporated in suitable tomato varieties through breeding. This allows the growers to obtain a good yield even when a certain virus is present during production. Regularly however new viruses or strains of known viruses are identified, that in certain instances can break the available resistance.

In 2015 the occurrence of a new tobamovirus in tomato was published (Salem et al: A new tobamovirus infecting tomato crops in Jordan. Arch Virol. 2016 February; 161(2): 503-6. Epub 2015 Nov. 19). This virus was shown to be related to the known tobamoviruses Tobacco mosaic virus (TMV), Tomato mosaic virus (ToMV), and Tomato mild mottle virus (ToMMV), with sequence identities of around 80% to 90% for the closest related sequences of ToMMV and ToMV. Symptoms were rather mild on the plant, but very severe brown rugose symptoms were present on almost all fruits. The virus was observed to break the resistance of the commonly used resistance genes against ToMV: Tm-1, Tm-2, and Tm-$2^2$, which is also known as Tm-$2^a$. A later publication showed that the virus was also found in Israel, and it was established that the virus can also infect pepper (*Capsicum annuum*) plants (Luria et al (2017): A new Israeli tobamovirus isolate infects tomato plants harboring Tm-$2^2$ resistance genes. PLoS ONE 12(1):e0170429. Doi:10.1371/journal.pone.0170429). Symptoms appeared to vary based on the affected variety, and in certain instances symptoms were mainly found on the vegetative parts in the form of severe or mild mosaic, necrosis, leaf distortion, or other symptoms. As the virus was clearly different from the known tobamoviruses it was described with a new designation: Tomato brown rugose fruit virus (TBRFV).

Because of the severity of the symptoms on the fruits the impact of the presence of TBRFV on tomato growers is very high, since it leaves the fruits basically unmarketable. No resistance against the virus has been identified so far. The virus is at least transmitted mechanically, which makes the spread easy and rapid, and difficult to control. Transmission of the virus is also likely to occur through infected seed.

Citation or identification of any document in this application is not an admission that such document is available as prior art to the present invention.

SUMMARY OF THE INVENTION

It is an object of the present invention to provide a tomato plant of the species *Solanum lycopersicum* that is resistant to Tomato brown rugose fruit virus (TBRFV).

Because the problems with the new TBRFV spread very quickly and had a major effect on tomato production in certain areas, the urgency to obtain resistant tomato plants was very high. In addition, the virus was expected to be able to spread rapidly to other areas due to its very effective transmission. A large germplasm screen was therefore organized to get an insight in the presence of possible sources.

*Solanum lycopersicum* has various wild relatives that harbor disease resistances and are a valuable resource for breeding. Many of the latest tomato varieties therefore already possess one or more introgressions from wild species. However, it appeared that presently cultivated tomato varieties, including the ones that already have tobamovirus resistance genes from wild relatives, were easily infected by this new virus. This could mean it would not be straightforward to identify resistance.

Surprisingly, after extensive screening, three accessions of the species *Solanum pimpinellifolium* could be identified that were highly resistant to TBRFV (Example 1). A research program was subsequently set up to determine if the resistance could be transferred to *Solanum lycopersicum*, and to identify the genetics behind the resistance.

Crosses were made between the three *S. pimpinellifolium* sources GNL.3919, GNL.3920, and GNL.3951 on the one hand, and internal breeding lines, followed by population development, such as F2, F3, and backcross populations, for QTL mapping. On all generations bio-assays were carried out to confirm and monitor the resistance in the various populations, and to determine the inheritance. The identification and characterization of a QTL through molecular markers gives the opportunity to use genetically linked markers to identify the presence of the QTL and therefore the presence of the resistance, which is obviously much more efficient than the use of a bio-assay.

For this purpose QTL mapping studies were performed. A first QTL mapping on F2 populations identified a QTL region on chromosome 11 that was present in populations that were developed based on all three *S. pimpinellifolium* sources.

The present invention provides a tomato plant that is resistant to Tomato brown rugose fruit virus (TBRFV), which plant comprises a QTL on chromosome 11. The QTL on chromosome 11 is in particular a QTL derived from or introgressed from the species *S. pimpinellifolium*.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

Seed of tomato *Solanum lycopersicum* comprising the QTL of the invention on chromosome 11 homozygously, resulting in a TBRFV resistant plant, was deposited with NCIMB Ltd, Ferguson Building, Craibstone Estate, Bucksburn, Aberdeen AB21 9YA, UK on Sep. 11, 2017 under deposit accession numbers NCIMB 42882, NCIMB 42885, NCIMB 42887, and NCIMB 42890.

The Deposits with NCIMB Ltd, under deposit accession numbers NCIMB 42882, NCIMB 42885, NCIMB 42887, and NCIMB 42890 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1—Nucleotide sequences of SEQ ID NOS: 1 to 53.

DETAILED DESCRIPTION OF THE INVENTION

The present invention provides a tomato plant that is resistant to Tomato brown rugose fruit virus (TBRFV), which plant comprises a QTL on chromosome 11. The QTL on chromosome 11 is in particular a QTL derived from or introgressed from the species *S. pimpinellifolium*.

The QTL on chromosome 11 is located between SEQ ID NO: 1 and SEQ ID NO: 53. The QTL of the invention is in order of increased preference flanked by SEQ ID NO: 4 and SEQ ID NO: 52, by SEQ ID NO: 5 and SEQ ID NO: 52, by SEQ ID NO: 5 and SEQ ID NO: 51, by SEQ ID NO: 4 and SEQ ID NO: 33, by SEQ ID NO: 5 and SEQ ID NO: 11, or by SEQ ID NO: 6 and SEQ ID NO: 11, or by SEQ ID NO: 7 and SEQ ID NO: 11. The QTL of the invention on chromosome 11 is most preferably flanked by SEQ ID NO: 8 and SEQ ID NO: 10. As used herein, flanked by means that the sequences represent the borders of the QTL region and are therefore thus part of the QTL.

A marker for identification of the presence of the QTL of the invention on chromosome 11 is in order of increased preference selected from the group comprising SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11. A marker for identification of the QTL of the invention is most preferably selected from the group comprising SEQ ID NOS: 8 to 10. As used herein, a marker for identification of the QTL is a marker represented by a sequence in FIG. 1 that is present in the QTL.

A further marker for identification of the presence of the QTL of the invention can be based on any other polymorphism between a resistant plant of the invention and a susceptible control plant, wherein the polymorphism is in order of increased preference located between SEQ ID NO: 4 and SEQ ID NO: 52, or between SEQ ID NO: 5 and SEQ ID NO: 52, or between SEQ ID NO: 5 and SEQ ID NO: 51, or between SEQ ID NO: 4 and SEQ ID NO: 33, or between SEQ ID NO: 5 and SEQ ID NO: 11, or between SEQ ID NO: 6 and SEQ ID NO: 11. A further marker for identification of the presence of the QTL of the invention is most preferably based on any other polymorphism between a resistant plant of the invention and a susceptible plant, wherein the polymorphism is located between SEQ ID NO: 7 and SEQ ID NO: 11 (Example 2).

FIG. 1 gives the sequences of the SEQ ID NOS: that can be used as markers, or used to develop markers, to identify the presence of the QTL of the invention on chromosome 11 leading to TBRFV resistance in a tomato plant. Table 3 shows the marker score, i.e. the nucleotide in the sequence, that identifies the presence of the QTL, and therefore a resistant plant, as well as the position of the SNP in the sequence of FIG. 1. When the sequences of the markers are positioned on for example version SL3_00 of the publicly available genome reference sequence for *S. lycopersicum*, the physical position to which the SNP polymorphism in said marker sequence corresponds can be derived. This position is also presented in Table 3. Version SL3_00 of the public *S. lycopersicum* genome reference sequence can for example be accessed at the Solgenomics website (solgenomics.net) and is the reference for 'the public tomato genome' as used herein. The positions of the QTLs and the markers described in Luria et al (2017, supra). Observation of the symptoms on the young tomato plants can be done at around 12-18 days after inoculation (dai).

TBRFV resistance is determined by comparison to a control variety known to be TBRFV susceptible. Examples of TBRFV susceptible tomato varieties that can be used as control are Candela F1 and Razymo F1. Since no tomato varieties that are resistant to TBRFV were known before the invention, it was not possible to include a resistant control before the present invention was done. Resistance is suitably scored on a scale of 0-4; the scales of the scores can be found in Table 1.

TABLE 1 scales TBRFV resistance scores

| score | Symptoms |
|---|---|
| 0 | No symptoms |
| 1 | Not clean, a single spot, some minor discoloration |
| 2 | Mosaic, clear visible symptoms |
| 3 | Severe mosaic, starting deformation in the head |
| 4 | Severe mosaic, necrosis on the stem, serious deformation in the head, spots in blisters | of the invention are derivable from a public map and these positions are relative to said physical positions.

Identifying the presence of a marker is in particular done by identifying the presence of the nucleotide at the position of the SNP that is indicative for the resistance, as present in any of the sequences determining the SEQ ID NOS, as compared to the wildtype nucleotide at the position of the SNP; the locations and nucleotide of the SNPs that are genetically linked to and therefore indicative of resistance are indicated in Table 3. The wildtype nucleotide is the nucleotide that is present on that position in the public genome.

As used herein, a tomato plant is a plant of the species *Solanum lycopersicum*.

As used herein, resistance to the Tomato brown rugose fruit virus is resistance to the virus as described in Salem et al (2016, supra), which virus was assigned NCBI Taxonomy ID 1761477.

As used herein a marker is genetically linked to, and can therefore be used for the identification of, the QTL of the invention, when the marker and the TBRFV resistance co-segregate in a segregating population resulting from a cross between a plant comprising the QTL of the invention and a plant lacking the QTL.

TBRFV resistance of the present invention inherits in an intermediate manner. As used herein, intermediate means that when the QTL of the invention is homozygously present, it gives a higher level of TBRFV resistance than when the QTL of the invention is heterozygously present. The heterozygous presence of the QTL of the invention however still confers a certain level of TBRFV resistance, which can be defined as tolerance. The TBRFV resistance of both homozygous and heterozygous plants makes the plants more suitable for cultivation under conditions where TBRFV is present. Therefore both levels of resistance are considered to be improved agronomic characteristics. The highest level of resistance is obtained when the QTL is homozygously present.

The presence of TBRFV resistance can be determined through a bioassay, for example using a standard sap-mechanical inoculation technique for tobamoviruses, which is known to the skilled person, and is also for example As used herein, a TBRFV resistant tomato plant wherein the QTL is present homozygously has a score of 0 or 1, or at the most a score lower than 2, when scoring according to Table 1 is used. A tolerant plant has a score lower than 3.

A *S. lycopersicum* plant that has the QTL of the invention that leads to TBRFV resistance can be grown from seed deposited as NCIMB 42882, NCIMB 42885, NCIMB 42887, or NCIMB 42890. NCIMB 42882 was developed from GNL.3951. NCIMB 42885 was developed from GBN.3920. NCIMB 42887 and NCIMB 42890 were developed from GNL.3919.

NCIMB 42882 has the TBRFV resistance of the invention and comprises the QTL of the invention on chromosome 11 that is in order of increased preference located between SEQ ID NOS: 1 and 53, or between SEQ ID NO: 4 and SEQ ID NO: 52, or between SEQ ID NO: 5 and SEQ ID NO: 52, or between SEQ ID NO: 5 and SEQ ID NO: 51, or between SEQ ID NO: 4 and SEQ ID NO: 33, or between SEQ ID NO: 5 and SEQ ID NO: 11, or between SEQ ID NO: 6 and SEQ ID NO: 11. The QTL of the invention in NCIMB 42882 is most preferably located between SEQ ID NO: 7 and SEQ ID NO: 11. The QTL is present in the deposit NCIMB 42882 in homozygous form.

NCIMB 42885 has the TBRFV resistance of the invention and comprises the QTL of the invention on chromosome 11 that is in order of increased preference located between SEQ ID NOS: 1 and 53, or between SEQ ID NO: 4 and SEQ ID NO: 52, or between SEQ ID NO: 5 and SEQ ID NO: 52, or between SEQ ID NO: 5 and SEQ ID NO: 51, or between SEQ ID NO: 4 and SEQ ID NO: 33, or between SEQ ID NO: 5 and SEQ ID NO: 11, or between SEQ ID NO: 6 and SEQ ID NO: 11. The QTL of the invention in NCIMB 42885 is most preferably located between SEQ ID NO: 7 and SEQ ID NO: 11. The QTL is present in the deposit NCIMB 42885 in homozygous form.

NCIMB 42887 has the TBRFV resistance of the invention and comprises the QTL of the invention on chromosome 11 that is in order of increased preference located between SEQ ID NOS: 1 and 53, or between SEQ ID NO: 4 and SEQ ID NO: 52, or between SEQ ID NO: 5 and SEQ ID NO: 52, or between SEQ ID NO: 5 and SEQ ID NO: 51, or between SEQ ID NO: 4 and SEQ ID NO: 33, or between SEQ ID NO:

5 and SEQ ID NO: 11, or between SEQ ID NO: 6 and SEQ ID NO: 11. The QTL of the invention in NCIMB 42887 is most preferably located between SEQ ID NO: 7 and SEQ ID NO: 11. The QTL is present in the deposit NCIMB 42887 in homozygous form.

NCIMB 42890 has the TBRFV resistance of the invention and comprises the QTL of the invention on chromosome 11 that is in order of increased preference located between SEQ ID NOS: 1 and 53, or between SEQ ID NO: 4 and SEQ ID NO: 52, or between SEQ ID NO: 5 and SEQ ID NO: 52, or between SEQ ID NO: 5 and SEQ ID NO: 51, or between SEQ ID NO: 4 and SEQ ID NO: 33, or between SEQ ID NO: 5 and SEQ ID NO: 11, or between SEQ ID NO: 6 and SEQ ID NO: 11. The QTL of the invention in NCIMB 42890 is most preferably located between SEQ ID NO: 7 and SEQ ID NO: 11. The QTL is present in the deposit NCIMB 42890 in homozygous form.

A plant comprising the QTL of the invention on chromosome 11 can be used as a resistant control variety in a TBRFV bio-assay. When a plant, line, or population to be assessed shows the same level of resistance as NCIMB 42882, NCIMB 42885, NCIMB 42887, or NCIMB 42890 in a bio-assay, and this plant, line or population comprises the QTL as described herein on chromosome 11, this plant, line, or population is considered to have the TBRFV resistance of the invention and is therefore a plant of the invention.

A plant of the present invention is optionally a cultivated *S. lycopersicum* plant having improved agronomic characteristics that make it suitable for commercial cultivation. The invention also relates to a tomato fruit harvested from a plant of the invention, wherein the tomato fruit comprises the QTL of the invention in its genome which leads to TBRFV resistance in the plant. This tomato fruit is also referred to herein as 'the fruit of the invention' or 'the tomato fruit of the invention'. As used herein, 'tomato fruit' comprises a fruit produced by a plant of the species *Solanum lycopersicum*.

The present invention provides a QTL on chromosome 11, which QTL is genetically linked to at least one of the markers selected from the group comprising in order of increased preference SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11, wherein the presence of said QTL in a *S. lycopersicum* plant leads to TBRFV resistance. The QTL of the invention is most preferably genetically linked to at least one of the markers selected from the group comprising SEQ ID NOS: 8 to 10.

The present invention relates to a method for producing a TBRFV resistant *S. lycopersicum* plant comprising introducing a QTL on chromosome 11, wherein the QTL region in order of increased preference is flanked by SEQ ID NO: 4 and SEQ ID NO: 52, or flanked by SEQ ID NO: 5 and SEQ ID NO: 52, or flanked by SEQ ID NO: 5 and SEQ ID NO: 51, or flanked by SEQ ID NO: 4 and SEQ ID NO: 33, or flanked by SEQ ID NO: 5 and SEQ ID NO: 11, or flanked or by SEQ ID NO: 6 and SEQ ID NO: 11, or flanked by SEQ ID NO: 7 and SEQ ID NO: 11 in a *S. lycopersicum* plant. Most preferably the QTL that is introduced is flanked by SEQ ID NO: 8 and SEQ ID NO: 10.

The QTL of the invention can be introduced from another plant which comprises the QTL through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cis-genesis can be applied. Suitably markers as described herein are used to follow the incorporation of the QTL into another plant.

The above method can in particular be used to introduce the QTL of the invention into a plant species that is suitable for incorporation of such genetic information. In a particular embodiment said QTL can be introduced from a *Solanum pimpinellifolium* plant comprising the QTL into a *Solanum lycopersicum* plant lacking the QTL, for example by using standard breeding methods. In another embodiment said QTL can be introduced from a *Solanum lycopersicum* plant comprising the QTL into a *Solanum lycopersicum* plant lacking the QTL using standard breeding methods.

The QTL on chromosome 11 can be introduced from a *Solanum lycopersicum* plant representative seed of which was deposited with the NCIMB under deposit number NCIMB 42882, NCIMB 42885, NCIMB 42887, or NCIMB 42890, or from the deposited seed of NCIMB 42882, NCIMB 42885, NCIMB 42887, or NCIMB 42890, or from sexual or vegetative descendants thereof. Introduction of the QTL on chromosome 11 in *Solanum lycopersicum* leads to TBRFV resistance.

Alternatively the QTL of the invention can be transferred or introduced from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention.

The invention further relates to a plant of the invention comprising the QTL of the invention leading to TBRFV resistance either homozygously or heterozygously, which plant is a plant of an inbred line, a hybrid, a doubled haploid, or a plant of a segregating population. Preferably, the plant of the invention is a non-transgenic plant.

The invention also relates to a *Solanum lycopersicum* seed comprising the QTL of the invention on chromosome 11, wherein the plant grown from the seed is a plant of the invention that is resistant to TBRFV. The invention also relates to seed produced by a plant of the invention wherein the seed harbors the QTL of the invention, and as such, a plant grown from said seed is a plant of the invention.

Moreover, the invention also relates to a food product or a processed food product comprising the tomato fruit of the invention or part thereof. The food product may have undergone one or more processing steps. Such a processing step might comprise but is not limited to any one of the following treatments or combinations thereof: peeling, cutting, washing, juicing, cooking, cooling or a salad mixture comprising the fruit of the invention. The processed form that is obtained is also part of this invention.

The invention also relates to propagation material suitable for producing a *Solanum lycopersicum* plant of the invention, wherein the propagation material is suitable for sexual reproduction, and is in particular selected from a microspore, pollen, an ovary, an ovule, an embryo sac, and an egg cell; or is suitable for vegetative reproduction, and is in particular selected from a cutting, a root, a stem, a cell, a protoplast; or is suitable for tissue culture of regenerable cells, and is in particular selected from a leaf, pollen, an embryo, a cotyledon, a hypocotyl, a meristematic cell, a root, a root tip, an anther, a flower, a seed, and a stem; wherein the plant produced from the propagation material comprises the QTL of the invention on chromosome 11 as defined herein that confers TBRFV resistance. A plant of the invention may be used as a source of the propagation material.

The invention further relates to a cell comprising the QTL of the invention as defined herein. A cell of the invention can be obtained from, or be present in, a plant of the invention. Such a cell may either be in isolated form, or a part of a complete plant, or from a part thereof, and still constitutes a cell of the invention because such a cell comprises the genetic information that determines the QTL as described herein that leads to TBRFV resistance of a cultivated *S. lycopersicum* plant. Each cell of a plant of the invention carries the genetic information that leads to TBRFV resistance. A cell of the invention may also be a regenerable cell that can regenerate into a new plant of the invention. The presence of the genetic information in this context is the presence of the QTL of the invention on chromosome 11, wherein the QTL is as defined herein.

The invention further relates to plant tissue of a plant of the invention, which comprises the QTL of the invention on chromosome 11 as defined herein. The tissue can be undifferentiated tissue or already differentiated tissue. Undifferentiated tissue is for example a stem tip, an anther, a petal, pollen, and can be used in micropropagation to obtain new plantlets that are grown into new plants of the invention. The tissue can also be grown from a cell of the invention.

The invention moreover relates to progeny of a plant, a cell, a tissue, or a seed of the invention, which progeny comprises the QTL of the invention on chromosome 11 as defined herein, the presence of which QTL, preferably in homozygous form, leads to TBRFV resistance. Such progeny can in itself be a plant, a cutting, a seed, a cell, or a tissue.

As used herein "progeny" is intended to mean the first and all further descendants from a cross with a plant of the invention, wherein a cross comprises a cross with itself or a cross with another plant, and wherein a descendant that is determined to be progeny comprises the QTL of the invention on chromosome 11 as defined herein that leads to resistance to TBRFV. The plant of the invention that is used in this cross is optionally a plant of deposit NCIMB 42882, NCIMB 42885, NCIMB 42887, NCIMB 42890, or progeny seed thereof which is a direct or further descendant through crossing a plant grown from the deposited seed with itself or with another plant for one or more subsequent generations.

"Progeny" also encompasses a *S. lycopersicum* plant that carries the QTL of the invention on chromosome 11 and is resistant to TBRFV, and is obtained from another plant, or progeny of a plant, of the invention by vegetative propagation or another form of multiplication.

The invention further relates to a part of a *S. lycopersicum* plant of the invention that is suitable for sexual reproduction, which plant part comprises the QTL of the invention on chromosome 11, which QTL is as defined herein. Such a part is for example selected from the group comprising a microspore, a pollen, an ovary, an ovule, an embryo sac, and an egg cell.

Additionally, the invention relates to a part of a *S. lycopersicum* plant of the invention that is suitable for vegetative reproduction, which is in particular a cutting, a root, a stem, a cell, or a protoplast that comprises the QTL of the invention on chromosome 11, which QTL is as defined herein. A part of a plant as previously mentioned is considered propagation material. The plant that is produced from the propagation material comprises the QTL of the invention on chromosome 11 as defined herein, the presence of which QTL leads to TBRFV resistance.

The invention further relates to tissue culture of a plant of the invention, which is also propagation material and which comprises the QTL of the invention on chromosome 11 in its genome, which QTL is as defined herein. The tissue culture comprises regenerable cells. Such tissue culture can be selected or derived from any part of the plant, in particular from a leaf, pollen, an embryo, a cotyledon, a hypocotyl, a meristematic cell, a root, a root tip, an anther, a flower, a seed, or a stem. The tissue culture can be regenerated into a *S. lycopersicum* plant comprising the QTL of the invention on chromosome 11 as defined herein, wherein the regenerated *S. lycopersicum* plant expresses TBRFV resistance and is also part of the invention.

The invention additionally relates to the use of a plant of the invention in plant breeding. The invention thus also relates to a breeding method for the development of a cultivated *S. lycopersicum* plant that is resistant to TBRFV, wherein a plant comprising the QTL of the invention on chromosome 11 as defined herein for conferring said resistance to another plant is used. Seed being representative for a plant that can be used in plant breeding to develop another plant with TBRFV resistance was deposited with the NCIMB under accession numbers NCIMB 42882, NCIMB 42885, NCIMB 42887, and NCIMB 42890.

The invention also concerns the use of the QTL of the invention on chromosome 11 as defined herein for the development of a *Solanum lycopersicum* plant that has resistance to TBRFV.

The invention also relates to a marker for the identification of TBRFV resistance in a *Solanum lycopersicum* plant, which marker is in order of increased preference selected from the group comprising SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11 for the identification of the QTL on chromosome 11. A marker for identification of the QTL of the invention is most preferably selected from the group comprising SEQ ID NOS: 8 to 10. Any other marker that is developed based on a polymorphism in any of the regions as defined above between said SEQ ID NOS: is also part of the invention.

The use of any of the markers from the group comprising SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11, or most preferably from the group comprising SEQ ID NOS: 8 to 10 for identification of TBRFV resistance in a *Solanum lycopersicum* plant is also part of the invention. Any of these markers can also be used to develop other markers for the identification of the QTL on chromosome 11 leading to TBRFV resistance, by determining any other polymorphism in the regions between said SEQ ID NOS:, which use is also part of the present invention.

The present invention also relates to a method for selecting a TBRFV resistant *Solanum lycopersicum* plant, comprising identifying the presence of the QTL of the invention on chromosome 11, and selecting a plant that comprises said QTL as a TBRFV resistant plant.

Identifying the presence of the QTL on chromosome 11 is suitably done using a marker selected from the group comprising SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11, or most preferably from the group comprising SEQ ID NOS: 8 to 10.

The invention also relates to a method of testing a *Solanum lycopersicum* plant for the presence in its genome of the QTL of the invention on chromosome 11 conferring TBRFV resistance, comprising detecting the presence of a marker sequence selected from the group consisting of SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11, or most preferably from the group comprising SEQ ID NOS: 8 to 10 in the genome of the *Solanum lycopersicum* plant.

The method of testing a *Solanum lycopersicum* plant for the presence in its genome of the QTL of the invention on chromosome 11 conferring TBRFV resistance optionally further comprises selecting a *Solanum lycopersicum* plant that comprises said QTL as a TBRFV resistant plant.

The invention also relates to a method for the production of a *Solanum lycopersicum* plant which is resistant to TBRFV, said method comprising:
a) crossing a plant of the invention, which comprises the QTL of the invention on chromosome 11, with another plant;
b) optionally performing one or more rounds of selfing and/or crossing of the plant resulting from the cross to obtain a further generation population;
c) selecting from the plant resulting from the cross, or from the further generation population, a plant that comprises the QTL on chromosome 11 as defined herein, which plant is resistant against TBRFV.

Selection of a plant comprising the QTL on chromosome 11 is suitably done by using a molecular marker genetically linked to the QTL, which marker is selected from the group comprising SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11, or most preferably from the group comprising SEQ ID NOS: 8 to 10 for the identification of the QTL on chromosome 11. The plant can alternatively, or in addition, be phenotypically selected for having resistance to TBRFV, in particular by performing a bio-assay for TBRFV resistance.

In one embodiment of the invention, the plant of the invention used in the method for the production of a *Solanum lycopersicum* plant which is resistant against TBRFV is a plant grown from seed deposited under NCIMB accession number NCIMB 42882, NCIMB 42885, NCIMB 42887, or NCIMB 42890, or a progeny plant thereof which is a direct or further descendant through crossing a plant grown from the deposited seed with itself or with another plant for one or more subsequent generations.

The invention additionally provides for a method of introducing another desired trait into a *Solanum lycopersicum* plant comprising TBRFV resistance, comprising:
a) crossing a *Solanum lycopersicum* plant of the invention comprising the QTL on chromosome 11 with a second *Solanum lycopersicum* plant that comprises the other desired trait to produce F1 progeny;
b) optionally selecting in the F1 for a plant that comprises TBRFV resistance and the other desired trait;
c) crossing the optionally selected F1 progeny with either parent, to produce backcross progeny;
d) selecting backcross progeny comprising TBRFV resistance and the other desired trait; and
e) optionally repeating steps c) and d) one or more times in succession to produce selected fourth or higher backcross progeny that comprises the other desired trait and has resistance to TBRFV. Backcrossing is optionally done until the backcross progeny is stable and can be used as a parent line, which can be reached after up to 10 backcrosses.

In one embodiment of the invention, the plant of the invention used in the method of introducing another desired trait into a *Solanum lycopersicum* plant comprising resistance to TBRFV is a plant grown from seed deposited under NCIMB accession number NCIMB 42882, NCIMB 42885, NCIMB 42887, or NCIMB 42890, or a progeny plant thereof which is a direct or further descendant through crossing a plant grown from the deposited seed with itself or with another plant for one or more subsequent generations.

Optionally, selfing steps are performed after any of the crossing or backcrossing steps. Selection of a plant comprising the QTL of the invention on chromosome 11 that leads to TBRFV resistance and the other desired trait can alternatively be done following any crossing or selfing step of the method. The other desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a *Solanum lycopersicum* plant produced by this method and the *Solanum lycopersicum* fruit obtained therefrom.

The invention further relates to a method for the production of a *Solanum lycopersicum* plant comprising the QTL of the invention on chromosome 11, wherein the presence of the QTL leads to resistance to TBRFV, by using tissue culture of plant material that comprises the QTL of the invention in its genome.

The invention further relates to a method for the production of a *Solanum lycopersicum* plant comprising the QTL of the invention on chromosome 11, wherein the presence of said QTL leads to resistance to TBRFV, by using vegetative reproduction of plant material that comprises the QTL of the invention in its genome.

The invention further provides a method for the production of a *Solanum lycopersicum* plant comprising the QTL of the invention on chromosome 11 and having resistance to TBRFV as defined herein by using a doubled haploid generation technique to generate a doubled haploid line that homozygously comprises the QTL of the invention and is resistant against TBRFV.

The invention further relates to a method for the production of a *Solanum lycopersicum* plant comprising the QTL of the invention on chromosome 11 as defined herein, wherein the presence of said QTL leads to TBRFV resistance, which method comprises growing a seed comprising said QTL into the said *Solanum lycopersicum* plant. In one embodiment, the seed used in the method is seed deposited with the NCIMB under deposit number NCIMB 42882, NCIMB 42885, NCIMB 42887, or NCIMB 42890, or progeny seed thereof which is a direct or further descendant through crossing a plant grown from the deposited seed with itself or with another plant for one or more subsequent generations.

The invention further relates to a method for seed production comprising growing a Solanum lycopersicum plant from a seed of the invention, allowing the plant to produce a fruit with seed, harvesting the fruit, and extracting those seed. Production of the seed is suitably done by crossing with itself or with another plant that is optionally also a plant of the invention. The seed that is so produced has the capability to grow into a plant that comprises the QTL of the invention and is resistant to TBRFV.

The invention further relates to hybrid seed and to a method for producing said hybrid seed, comprising crossing a first parent plant with a second parent plant and harvesting the resultant hybrid seed, wherein the first parent plant and/or the second parent plant is a plant of the invention comprising the QTL of the invention on chromosome 11 as defined herein. The resulting hybrid plant that can be grown from the hybrid seed, comprising said QTL, which hybrid plant has resistance to TBRFV, is also a plant of the invention.

The parent that provides the TBRFV resistance of the invention can be a plant grown directly from the deposited seed. The parent can also be a progeny plant from the deposited seed which is a direct or further descendant obtained by crossing with itself or with another plant one or more times, or a progeny plant from seed that is identified to have obtained the QTL of the invention and thereby the TBRFV resistance of the invention by other means.

Introgression of the QTL of the invention on chromosome 11 as used herein means introduction of the QTL from a donor plant comprising said QTL into a recipient plant not carrying said QTL by standard breeding techniques, wherein selection for plants comprising the QTL of the invention can be performed phenotypically by means of observation of the resistance to TBRFV, or selection can be performed with the use of markers as defined herein, preferably a marker selected from the group comprising SEQ ID NOS: 4 to 52, or from the group comprising SEQ ID NOS: 5 to 52, or from the group comprising SEQ ID NOS: 5 to 51, or from the group comprising SEQ ID NOS: 4 to 33, or from the group comprising SEQ ID NOS: 5 to 11, or from the group comprising SEQ ID NOS: 6 to 11, or from the group comprising SEQ ID NOS: 7 to 11, or most preferably from the group comprising SEQ ID NOS: 8 to 10, through marker assisted breeding, or combinations of these selection methods. Selection is started in the F1 or any further generation from an initial cross between the recipient plant and the donor plant, followed by either further crossing with itself or with another plant, suitably by using markers as identified and defined herein. The skilled person is familiar with creating and using new molecular markers that can be used to identify or are genetically linked to the QTL and therefore the TBRFV resistance of the invention. Development and use of such markers for identification and selection of plants of the invention is also part of the invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Bio-Assay for TBRFV Resistance and Deposit Development in S. lycopersicum Because of increasing problems due to the presence of the new TBRFV tobamovirus, and the threat that this virus may easily spread over large areas, an extensive germplasm screen was organised. The screen for potentially resistant material was done through a bio-assay. Since the virus is mechanically transmitted, a standard mechanical inoculation technique was used in the bio-assay. No resistant material was known at the time, so it was not possible to include resistant controls. Susceptible controls were however easy to include; Candela F1 was included as it was published to be susceptible, and Razymo F1 was also included as a second susceptible control. To determine if perhaps resistance was already present in cultivated material, a large number of commercially available hybrid tomato varieties was also included.

Seed of the accessions to be tested was sown in standard seedling trays and 11 seedlings per accession were inoculated 3 weeks after sowing. Scoring of the symptoms was done according to Table 1; at 2 weeks after inoculation, and again at 3 weeks after inoculation.

Inoculum was prepared by grounding leaves of tomato plants that were infected with TBRFV in a 0.01 M phosphate buffer (pH 7.0) mixed with celite. Plants were dusted with carborundum powder prior to gently rubbing the leaf with inoculum.

In the large screen, three Solanum pimpinellifolium accessions GNL.3919, GNL.3920, and GNL.3951, were identified to be resistant to TBRFV. All three accessions were 100% resistant, showing no symptoms so having score 0, in the first as well as the second observation. For Candela F1 and Razymo F1, all plants had a score of 4, and they are therefore highly susceptible. The other commercial tomato varieties that were included had mainly scores 3 and 4, and none showed resistant plants.

The identified resistant S. pimpinellifolium sources were crossed with internal S. lycopersicum lines TB1, TB2, and TO1. F1 plants from these crosses were subsequently grown and F2 seeds were also obtained. A new large screen was set-up again including the sources, the breeding lines, the F1's and 184 F2 plants per population. Average scores of parents and F1's of this screen at two weeks after inoculation can be found in Table 2. The scores of the individual F2 plants segregated as expected and therefore ranged from scores 0 to 4. When plants scored a 3 at the first observation, as was the case for the internal breeding lines TB1, TB2, and T01, the plants were removed and a second observation was not done.

From the segregating F2 populations resistant plants were chosen and selfed. Using the parallel developed markers from the QTL analysis (see Example 2), plants were selected that had the identified QTL. Seeds from these individual plants, in which all three sources were represented, were subsequently deposited as NCIMB 42882, NCIMB 42885, NCIMB 42887, and NCIMB 42890. NCIMB 42882 was developed from a cross with GNL.3951. NCIMB 42885 was developed from a cross with GNL.3920. NCIMB 42887 and NCIMB 42890 were developed from crosses with GNL.3919. All deposited plants have the QTL on chromosome 11 homozygously.

TABLE 2

TBRFV bio-assay results

| Number | | Average line or F1 score |
|---|---|---|
| TB1 | F8 | 3 |
| TB2 | F9 | 3 |
| TO1 | F9 | 3 |
| GNL.3920 | F6 | 0.5 |
| GNL.3951 | F6 | 0.5 |
| GNL.3919 | F6 | 0.5 |
| (TB1 × GNL.3920) | F1 | 1.0 |
| (TB2 × GNL.3920) | F1 | 3.0 |
| (TO1 × GNL.3920) | F1 | 0.5 |
| (TB1 × GNL.3951) | F1 | 1.0 |
| (TB2 × GNL.3951) | F1 | 3.5 |
| (TO1 × GNL.3951) | F1 | 1.5 |
| (TB1 × GNL.3919) | F1 | 0.5 |
| (TB2 × GNL.3919) | F1 | 2.4 |
| (TO1 × GNL.3919) | F1 | 0.5 |

Further observations were done on F2 and F3 plants that were selected to have the QTL homozygously, which confirmed that the presence of the QTL resulted in a disease score averaging 0-1, occasionally towards 1.5, according to the scale described in Table 1. Backcrosses were made with the breeding lines as recurrent parents, and also in subsequent selfed populations of the backcross generations the homozygous presence of the QTL was found to result in plants that were resistant to TBRFV.

Example 2: QTL Mapping and Marker Development

In order to map TBRFV resistance conferring QTLs from the identified sources, 184 plants of the F2 populations of 7 F1's from Table 2 were phenotyped for TBRFV resistance; parents were also included for reference; DNA samples were taken of each plant for genotyping. Phenotypic scores 0 to 4 according to Table 1 were present in all F2 populations.

Per population a genetic map was constructed; non-polymorphic markers and markers with a strong segregation distortion were removed. For each population around 400 to 450 markers were mapped that were well-distributed over the genome with an average spacing of 2-3 cM. The marker order was determined; the public genome assembly was used to determine numbering and orientation of the linkage groups. From the seven individual maps a consensus map was created.

Phenotypic scores, genotypic data, and a consensus map containing marker positions were used as input data for the QTL mapping. QTL analysis was performed, and mapping of the data initially resulted in the identification of three QTLs: one on chromosome 11, one on chromosome 12, and one on chromosome 6.

Through further observations on populations that segregated for resistance, and subsequent fine-mapping of the QTLs, it was found that the main contribution to resistance to TBRFV was due to the presence of the QTL on chromosome 11. Through this fine-mapping the QTL region on chromosome 11 could be further narrowed down. Identification of recombinants within the original QTL initially resulted in a smaller region of approximately 54 Mbp. Even further fine-mapping resulted in a small region comprising an introgression from the source between around 7.7 Mbp and 10.1 Mbp. The final recombinants that showed resistance only had a small introgression from the source between around 8.6 and 10.1 Mbp, which is between SEQ ID NO: 7 and SEQ ID NO: 10. The exact positions as based on the public SL3_00 tomato map can be found in Table 3. Polymorphic SNP markers that were identified in this analysis and that are present in the QTL region are presented in Table 3. The sequences of these markers are given in FIG. 1. These markers can be used to identify the presence of the QTL in plants grown from the deposits or in progeny thereof. These markers can further be used to identify the presence of the QTL of the invention for TBRFV resistance on chromosome 11 in any other population that comprises the QTL.

TABLE 3

| SNP markers - nucleotides and physical positions. | | | | | |
|---|---|---|---|---|---|
| Marker name | QTL on chromosome | position of the SNP in the sequence of FIG. 1 | Nucleotide of the SNP in FIG. 1, to be used as marker of the invention | Nucleotide of the SNP in the wildtype (susceptible allele) | physical position of the SNP marker on the public SL3_00 genome map (in bp) |
| SEQ ID NO: 1 | 11 | 101 | G | A | 500.502 |
| SEQ ID NO: 2 | 11 | 101 | T | C | 2.795.712 |
| SEQ ID NO: 3 | 11 | 101 | G | A | 4.361.048 |
| SEQ ID NO: 4 | 11 | 101 | G | A | 6.171.927 |
| SEQ ID NO: 5 | 11 | 101 | T | C | 7.767.493 |
| SEQ ID NO: 6 | 11 | 101 | G | A | 8.301.189 |
| SEQ ID NO: 7 | 11 | 101 | G | A | 8.646.415 |
| SEQ ID NO: 8 | 11 | 101 | A | G | 8.994.394 |
| SEQ ID NO: 9 | 11 | 101 | T | C | 9.277.404 |
| SEQ ID NO: 10 | 11 | 101 | T | C | 9.690.525 |
| SEQ ID NO: 11 | 11 | 101 | G | A | 10.160.922 |
| SEQ ID NO: 12 | 11 | 101 | G | A | 10.757.429 |
| SEQ ID NO: 13 | 11 | 101 | T | A | 11.047.902 |
| SEQ ID NO: 14 | 11 | 101 | C | T | 11.666.713 |
| SEQ ID NO: 15 | 11 | 101 | G | A | 12.754.076 |
| SEQ ID NO: 16 | 11 | 101 | C | T | 13.158.870 |
| SEQ ID NO: 17 | 11 | 101 | T | G | 14.111.302 |
| SEQ ID NO: 18 | 11 | 101 | T | C | 14.709.171 |

TABLE 3-continued SNP markers - nucleotides and physical positions.

| Marker name | QTL on chromosome | position of the SNP in the sequence of FIG. 1 | Nucleotide of the SNP in FIG. 1, to be used as marker of the invention | Nucleotide of the SNP in the wildtype (susceptible allele) | physical position of the SNP marker on the public SL3_00 genome map (in bp) |
|---|---|---|---|---|---|
| SEQ ID NO: 19 | 11 | 101 | A | C | 15.793.668 |
| SEQ ID NO: 20 | 11 | 51 | T | C | 16.743.861 |
| SEQ ID NO: 21 | 11 | 101 | C | T | 17.813.330 |
| SEQ ID NO: 22 | 11 | 101 | C | T | 18.035.442 |
| SEQ ID NO: 23 | 11 | 101 | A | C | 19.037.419 |
| SEQ ID NO: 24 | 11 | 101 | T | G | 19.861.485 |
| SEQ ID NO: 25 | 11 | 101 | A | G | 21.007.068 |
| SEQ ID NO: 26 | 11 | 101 | A | C | 22.005.271 |
| SEQ ID NO: 27 | 11 | 101 | A | G | 22.555.950 |
| SEQ ID NO: 28 | 11 | 101 | T | C | 23.000.281 |
| SEQ ID NO: 29 | 11 | 101 | G | A | 24.013.262 |
| SEQ ID NO: 30 | 11 | 101 | A | C | 25.017.391 |
| SEQ ID NO: 31 | 11 | 101 | T | C | 25.592.480 |
| SEQ ID NO: 32 | 11 | 101 | G | A | 26.642.083 |
| SEQ ID NO: 33 | 11 | 101 | A | G | 28.163.196 |
| SEQ ID NO: 34 | 11 | 101 | C | G | 29.162.083 |
| SEQ ID NO: 35 | 11 | 101 | C | T | 30.664.049 |
| SEQ ID NO: 36 | 11 | 101 | C | T | 33.366.572 |
| SEQ ID NO: 37 | 11 | 101 | A | G | 34.432.114 |
| SEQ ID NO: 38 | 11 | 101 | T | C | 35.256.037 |
| SEQ ID NO: 39 | 11 | 101 | T | A | 36.929.975 |
| SEQ ID NO: 40 | 11 | 101 | C | A | 37.207.298 |
| SEQ ID NO: 41 | 11 | 101 | C | T | 39.422.329 |
| SEQ ID NO: 42 | 11 | 101 | A | G | 40.717.481 |
| SEQ ID NO: 43 | 11 | 101 | G | A | 41.981.699 |
| SEQ ID NO: 44 | 11 | 101 | G | A | 42.823.983 |
| SEQ ID NO: 45 | 11 | 101 | C | T | 43.242.945 |
| SEQ ID NO: 46 | 11 | 101 | A | G | 45.293.083 |
| SEQ ID NO: 47 | 11 | 101 | T | G | 46.335.358 |
| SEQ ID NO: 48 | 11 | 101 | T | A | 47.501.022 |
| SEQ ID NO: 49 | 11 | 101 | A | C | 48.376.138 |
| SEQ ID NO: 50 | 11 | 101 | T | C | 49.586.501 |
| SEQ ID NO: 51 | 11 | 101 | C | T | 50.944.951 |
| SEQ ID NO: 52 | 11 | 61 | C | A | 51.797.680 |
| SEQ ID NO: 53 | 11 | 101 | A | G | 55.402.505 |

The invention is further described by the following numbered paragraphs:

1. A *Solanum lycopersicum* plant that is resistant to TBRFV, which plant comprises a QTL on chromosome 11, wherein the QTL on chromosome 11 is located between SEQ ID NO: 1 and SEQ ID NO: 53.

2. A *Solanum lycopersicum* plant of paragraph 1, wherein the presence of the QTL on chromosome 11 is identified by use of at least one of the markers selected from the group comprising SEQ ID NOS: 4 to 52.

3. A *Solanum lycopersicum* plant of paragraph 1 or 2, wherein the QTL is flanked by SEQ ID NO: 4 and SEQ ID NO: 52 in the genome of a *Solanum lycopersicum* plant representative seed of which was deposited with the NCIMB under deposit number NCIMB 42882, NCIMB 42885, NCIMB 42887, or NCIMB 42890.

4. A cell of a TBRFV resistant *Solanum lycopersicum* plant of any of the paragraphs 1-3, which cell comprises the QTL as defined in any of the paragraphs 1-3 on chromosome 11 in its genome.

5. A *Solanum lycopersicum* seed, wherein a plant grown from the seed is resistant to TBRFV due to the presence in its genome of the QTL on chromosome 11 as defined in any of the paragraphs 1-3.

6. Propagation material suitable for producing a *Solanum lycopersicum* plant of any one of the paragraphs 1-3, wherein the propagation material is suitable for sexual reproduction, and is in particular selected from the group comprising a microspore, pollen, an ovary, an ovule, an embryo sac, and an egg cell; or is suitable for vegetative reproduction, and is in particular selected from the group comprising a cutting, a root, a stem, a cell, and a protoplast; or is suitable for tissue culture of regenerable cells, and is in particular selected from the group comprising a leaf, pollen, an embryo, a cotyledon, a hypocotyl, a meristematic cell, a root, a root tip, an anther, a flower, a seed, and a stem; wherein the plant produced from the propagation material comprises the QTL that leads to TBRFV resistance on chromosome 11, as defined in any of the paragraphs 1-3.

7. Marker for the identification of TBRFV resistance in a *Solanum lycopersicum* plant, which marker is selected from the group comprising SEQ ID NOS: 4 to 52.

8. Marker for the identification of a QTL on chromosome 11 that leads to TBRFV resistance in a *Solanum lycopersicum* plant, which marker is selected from the group comprising SEQ ID NOS: 4 to 52.

9. Use of a marker of paragraph 7 or 8 for identification of TBRFV resistance in a *Solanum lycopersicum* plant.

10. Method for producing a TBRFV resistant *Solanum lycopersicum* plant comprising introducing a QTL as defined in any of the paragraphs 1-3 on chromosome 11, in a *S. lycopersicum* plant.

11. Method for selecting a TBRFV resistant *Solanum lycopersicum* plant, comprising identifying the presence of a QTL as defined in any of the paragraphs 1-3 on chromosome 11, and selecting a plant that comprises said QTL as a TBRFV resistant plant.

12. Method of paragraph 11, wherein identifying the presence of the QTL on chromosome 11 is done using a marker selected from the group comprising SEQ ID NOS: 4 to 52.

13. A method for the production of a *Solanum lycopersicum* plant which is resistant to TBRFV, said method comprising:
   a) crossing a plant of any one of the paragraphs 1-3 comprising the QTL on chromosome 11 with another plant;
   b) optionally performing one or more rounds of selfing and/or crossing of the plant resulting from the cross in step a) to obtain a further generation population;
   c) selecting from the plant resulting from the cross in step a), or from the further generation population of step b), a plant that comprises the QTL on chromosome 11, as defined in any of the paragraphs 1-3, which plant is resistant against TBRFV.

14. Method of paragraph 13, wherein selection of a plant comprising the QTL on chromosome 11 is done by using a molecular marker genetically linked to the QTL, which marker is selected from the group comprising SEQ ID NOS: 4 to 52.

15. Method of paragraph 13, wherein the plant which is resistant to TBRFV is phenotypically selected, in particular by using a bio-assay for TBRFV resistance.

16. Method of any of the paragraphs 13-15, wherein the plant of any of the paragraphs 1-3 is a plant grown from seed deposited under NCIMB accession number NCIMB 42882, NCIMB 42885, NCIMB 42887, or NCIMB 42890, or a progeny plant thereof.

17. Method for the production of hybrid seed comprising crossing a first parent plant with a second parent plant and harvesting the resultant hybrid seed, wherein the first parent plant and/or the second parent plant is a plant of the invention that is resistant to TBRFV comprising the QTL as defined in any of the paragraphs 1-3 on chromosome 11, wherein the presence of the QTL leads to resistance to TBRFV in the hybrid plant that is grown from the seed.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Solanum lycopersicum* plant that is resistant to Tomato brown rugose fruit virus (TBRFV),
   which plant comprises a QTL on chromosome 11,
   wherein the QTL on chromosome 11 is located between SEQ ID NO: 1 and SEQ ID NO: 53, and
   wherein the QTL on chromosome 11 is linked to a marker represented by SEQ ID NO. 9, and the QTL is as present in the genome of a *Solanum lycopersicum* plant representative seed of which was deposited with the NCIMB under deposit number NCIMB 42882, NCIMB 42885, NCIMB 42887, or NCIMB 42890.

2. A *Solanum lycopersicum* plant as claimed in claim 1, wherein the QTL is flanked by SEQ ID NO: 4 and SEQ ID NO: 52 in the genome of a *Solanum lycopersicum* plant representative seed of which was deposited with the NCIMB under deposit number NCIMB 42882, NCIMB 42885, NCIMB 42887, or NCIMB 42890.

3. A cell of a TBRFV resistant *Solanum lycopersicum* plant as claimed in claim 1, which cell comprises the QTL as defined in claim 1 on chromosome 11 in its genome.

4. A *Solanum lycopersicum* seed, wherein a plant grown from the seed is resistant to TBRFV due to the presence in its genome of the QTL on chromosome 11 as defined in claim 1.

5. A propagation material suitable for producing a *Solanum lycopersicum* plant as claimed in any claim 1,
   wherein the propagation material is suitable for sexual reproduction, vegetative reproduction or for tissue culture of regenerable cells,
   wherein the plant produced from the propagation material comprises the QTL that leads to TBRFV resistance on chromosome 11, as defined in claim 1.

6. The propagation material of claim 5, wherein the propagation material suitable for sexual reproduction is selected from the group comprising a microspore, pollen, an ovary, an ovule, an embryo sac, and an egg cell.

7. The propagation material of claim 5, wherein the propagation material suitable for vegetative reproduction is selected from the group consisting of a cutting, a root, a stem, a cell, and a protoplast.

8. The propagation material of claim 5, wherein the propagation material suitable for tissue culture of regenerable cells and is selected from the group comprising a leaf, pollen, an embryo, a cotyledon, a hypocotyl, a meristematic cell, a root, a root tip, an anther, a flower, a seed, and a stem.

9. A method for identifying TBRFV resistance in a *Solanum lycopersicum* plant comprising identifying a marker selected from the group consisting of SEQ ID NOS: 4 to 52 in the plant.

10. The method of claim 9 comprising identifying the marker represented by SEQ ID NO: 9 in the plant.

11. A method for producing a TBRFV resistant *Solanum lycopersicum* plant comprising introducing a QTL as defined in claim 1 on chromosome 11, in a *S. lycopersicum* plant.

12. A method for selecting a TBRFV resistant *Solanum lycopersicum* plant, comprising identifying the presence of a QTL as defined in claim 1 on chromosome 11, and selecting a plant that comprises said QTL as a TBRFV resistant plant.

13. The method as claimed in claim 12, wherein identifying the presence of the QTL on chromosome 11 is with a marker selected from the group consisting of SEQ ID NOS: 4 to 52.

14. A method for the production of a *Solanum lycopersicum* plant which is resistant to TBRFV, said method comprising:
    a) crossing the plant as claimed in claim 1 comprising the QTL on chromosome 11 with another plant;
    b) optionally performing one or more rounds of selfing and/or crossing of the plant resulting from the cross in step a) to obtain a further generation population;
    c) selecting from the plant resulting from the cross in step a), or from the further generation population of step b), a plant that comprises the QTL on chromosome 11, as defined in claim 1, which plant is resistant against TBRFV.

15. The method as claimed in claim 14, wherein selection of a plant comprising the QTL on chromosome 11 is with a molecular marker genetically linked to the QTL, which marker is represented by SEQ ID NO: 9.

16. The method as claimed in claim 14, wherein the plant which is resistant to TBRFV is phenotypically selected.

17. The method as claimed in claim 14, wherein the plant comprising the QTL from chromosome 11 from step a) is a plant grown from seed deposited under NCIMB accession number NCIMB 42882, NCIMB 42885, NCIMB 42887, or NCIMB 42890, or a progeny plant thereof.

18. A method for the production of hybrid seed comprising
    crossing a first parent plant with a second parent plant and harvesting the resultant hybrid seed,
    wherein the first parent plant and/or the second parent plant is a plant of the invention that is resistant to TBRFV comprising the QTL as defined in claim 1 on chromosome 11,
    wherein the presence of the QTL leads to resistance to TBRFV in the hybrid plant that is grown from the seed.

19. The method as claimed in claim 16, wherein the phenotypic selection is by an assay for TBRFV resistance.

* * * * *

SEQUENCE LISTING

```
<160> NUMBER OF SEQ ID NOS: 53

<210> SEQ ID NO 1
<211> LENGTH: 201
<212> TYPE: DNA
<213> ORGANISM: Solanum lycopersicum

<400> SEQUENCE: 1
tttatgggac gttgagcatc tcatgaactt acggagattt ctagttgagt tgtgtgatca        60
agtggtagat ttaacgttgt gtactatctc taaaagcttg gtcttaccaa gaggaattta       120
tcgtcttcct acacttgaag tcgagaattt ggaactgtct tatagtgata ttacaaccgc       180
gacatattca ttttactatg a                                                 201

<210> SEQ ID NO 2
<211> LENGTH: 201
<212> TYPE: DNA
<213> ORGANISM: Solanum lycopersicum

<400> SEQUENCE: 2
acacattaat aagtttcaag taccgataaa ggcaaatttt tatcatgggt tagcaaagca        60
agatgagtaa ggtatctgta gaattagata tactcaacca tgtctaaaag gtgtgtcact       120
ttcagatgcc tacatttacc gaaaaaagat aatcttgctt ttatgggctt taaccaaata       180
cacaagaatg ggatgcaaca g                                                 201

<210> SEQ ID NO 3
<211> LENGTH: 201
<212> TYPE: DNA
<213> ORGANISM: Solanum lycopersicum

<400> SEQUENCE: 3
agaaacaacc cctctaccta acacaaggta tgtgtaaggt ctaagtagac tctactatac        60
tagatatgtt attgttgttg agaaatgtaa tatgagggtc ggaaacatcc actctaccta       120
acacaaggta tgtgtaaggt ctacatagac tattatactg aatatgttat tgttgttgag       180
```

```
aaatgtaatc tgagggtcgg a                                            201
```

<210> SEQ ID NO 4
<211> LENGTH: 201
<212> TYPE: DNA
<213> ORGANISM: Solanum lycopersicum

<400> SEQUENCE: 4

```
gagagagcga atctgcaaag ctgatttccg atgctactgc ggctgctgga atgggtttga    60
ttgagctgag gaggattgaa gcttctagag aagttgctgg gactttggct aagactccta   120
atgttgctta cttgcctaag caagggaata tgcttcttgg actcggccgt tgagtaggta   180
atcaattgag caaaatgcta g                                            201
```

<210> SEQ ID NO 5
<211> LENGTH: 201
<212> TYPE: DNA
<213> ORGANISM: Solanum lycopersicum

<400> SEQUENCE: 5

```
ttgtagttaa ctaattaaat ttagaatmty catcctacaa cgcaagttaa aaacactcgt    60
aaatccggac acatgttgta ggattagggg tagatgtttt tgaggctatt aatagtgtag   120
agataaaagt tttggagtgt tttcaataca tctgtctygt tagaaaaagg tcgaggccca   180
cgttaaccgg ccattgtcac c                                            201
```

<210> SEQ ID NO 6
<211> LENGTH: 201
<212> TYPE: DNA
<213> ORGANISM: Solanum lycopersicum

<400> SEQUENCE: 6

```
gtttcattgt gttaagaatt gtgcctggga aaatgggtct ctgatggaat ggcaaaagaa    60
agtttatgtg ttactgaagc ttttcggtta ttgaagaaga ggaagaaaaa aactatatgg   120
ggagttcaca gcagtccggt agctttgggg accctcaaca aatctcctct gataatgtta   180
atggtctttg cttggctatt t                                            201
```

<210> SEQ ID NO 7
<211> LENGTH: 201
<212> TYPE: DNA
<213> ORGANISM: Solanum lycopersicum

<400> SEQUENCE: 7

```
tgagaagaaa agaagcagag ttcaatgtaa tgtcactaca actttcttta ttytgatctg    60
aaagattgtc agctccacaa acagtaccag acacagacac gactgccaca ttgattagga   120
aggacacaaa yaacgcgaaa ccgctctcta tcaagaagaa tttacatgca tcctacaaaa   180
tycaacatta attaattttt c                                            201
```

<210> SEQ ID NO 8
<211> LENGTH: 201
<212> TYPE: DNA
<213> ORGANISM: Solanum lycopersicum

<400> SEQUENCE: 8

```
agctactatc arttttccaa gaactttgct tctattgcaa ctcatttgac tagtctgact    60
cagaatgaag tgcctttagt tgtagtccga ccagtgaaaa aagagctttc aaaagcgcaa   120
```

```
gacattttg  actatgatcc  maacattagg  ggtggaaggt  aatgactaca  ttgtatrttg      180
tgatgcttca  catttgggtt  t                                                  201

<210> SEQ ID NO 9
<211> LENGTH: 201
<212> TYPE: DNA
<213> ORGANISM: Solanum lycopersicum

<400> SEQUENCE: 9
cactcgtgac  atgccttcac  ttcatccccg  ttacccctca  acttataaac  cccatattct      60
atctatcaag  acttataccc  gcttcagtac  cacatctttc  tgggtcaaca  ttacaacatg     120
tcaccacccc  catcctcaat  gacaatacac  atgaccatat  ttctaaaaca  caacaacacc     180 gagacttta  gtctccacct  a                                                   201

<210> SEQ ID NO 10
<211> LENGTH: 201
<212> TYPE: DNA
<213> ORGANISM: Solanum lycopersicum

<400> SEQUENCE: 10
attggtggta  atagagattc  tgtgactggt  ggtggtggtg  attctgtgay  tggtggagga      60
ggtgattytg  tgactggtgg  tggtggagat  gtaggctaat  ttgattttgg  ggaagatgga     120
gaagatgtag  acggtttgtt  tgtggttgat  tttcttcccc  ctgagcaggt  actgtatcaa     180
tgamagggtt  ctcttccccc  t                                                  201

<210> SEQ ID NO 11
<211> LENGTH: 201
<212> TYPE: DNA
<213> ORGANISM: Solanum lycopersicum

<400> SEQUENCE: 11
ttaagagttt  caatatcctt  tgtggtatcg  tcaagaaaat  cttgcagagc  agaaagattt      60
ttttggagag  attcgacatg  ttgttgtgta  caacttcgac  gaacgaaaga  ttggttaggt     120
ttgaagagtt  gttctaatgt  atacataagt  gaagaaagag  cagcataagc  catttctctt     180
aacaacaatt  attgctaaag  a                                                  201

<210> SEQ ID NO 12
<211> LENGTH: 201
<212> TYPE: DNA
<213> ORGANISM: Solanum lycopersicum

<400> SEQUENCE: 12
catcagattc  ctgcaaaata  taattacacc  tcacttaaga  agtacttgcc  tttaggtatg      60
aagccacctg  caatatattt  cagaaaaaac  agtgaaaagt  gacgagtcag  taaaaaaaat     120
gaaacaagag  tgtaaccaat  aaaattaaaa  aaattctcct  tctcacccat  gcgaaaagtg     180
ctgaaaaacc  aacaccaact  c                                                  201

<210> SEQ ID NO 13
<211> LENGTH: 201
<212> TYPE: DNA
<213> ORGANISM: Solanum lycopersicum

<400> SEQUENCE: 13
agtccttatc  tattattata  tggtgaacaa  gtcaataaaa  atactcgtaa  ttgaaatagt      60
tatcgataat  tgttcacttc  cctcttatgg  aattcgagtt  tacaattatg  atgtgttgtt     120
```

-continued

```
gaatagtgta agaattgatg catcatcact taaatatatt ctgttagaaa tattattgaa      180
ttcattgtac aatccatttg t                                                201

<210> SEQ ID NO 14
<211> LENGTH: 201
<212> TYPE: DNA
<213> ORGANISM: Solanum lycopersicum

<400> SEQUENCE: 14
ctcaatcgaa ggtactttgg aagtatcatc cctgagatgt gccaagaaag ctacacaacc      60
cttactcatc atcctgttag cacgaagaaa agagataata cgaactggag tggaaattta     120
gtcaccctcc cacactagcg gatctgtccc aggcttggcc aatattacag ttttagcatt     180
acaatctaag attgcaaaat t                                                201

<210> SEQ ID NO 15
<211> LENGTH: 201
<212> TYPE: DNA
<213> ORGANISM: Solanum lycopersicum

<400> SEQUENCE: 15
tcaaatcatc aagaaacgtc catgacgtca ggaaactagt tcaagaggtg ttgatgtgcg      60
ttagcctatt tgactaggtt ttaggagtca gaatttgatg gaattcggta gtaaggtgtc     120
taatacgtat tcgagttgtt ttatagtcaa aaattctggg tacgactctc caaggaccaa     180
ccaaagggcc cttgaggagg a                                                201

<210> SEQ ID NO 16
<211> LENGTH: 201
<212> TYPE: DNA
<213> ORGANISM: Solanum lycopersicum

<400> SEQUENCE: 16
aattggcctt tcctctttct agttgaaaaa aaaaacaaaa caagaggta tatgcaccaa       60 ttaacatcaa ttgtgaattc accagtgacg atatctactt caaaagatgt ttgtcttcta     120
ctgaatacag gatatgaatt aaattttcta gctccaagac accaatttag cataactata     180
kttataatac tacaaaaaaa a                                                201

<210> SEQ ID NO 17
<211> LENGTH: 201
<212> TYPE: DNA
<213> ORGANISM: Solanum lycopersicum

<400> SEQUENCE: 17
aacaaacaat acgaaactct atgcctaaaa atacacatat caacgaaact gacataacat      60
atctcccatt gatttttaaaa ttgttgaaaa tgcttacaat tgttaattcc actagatttg    120
agagtagaca aacaattaat gaaactcaat tcctaaaata cacatgaaaa ttaccataac     180
tatataaata aggtgatttt t                                                201

<210> SEQ ID NO 18
<211> LENGTH: 201
<212> TYPE: DNA
<213> ORGANISM: Solanum lycopersicum

<400> SEQUENCE: 18
gcattaaaat ccattgcatt actaatgcat agaactccat ggtattagta atatgctaat      60
```

```
gcatgcatta gaatccattg cactactaat gcatagaact tcatggtatt aataatactc    120
ttcaatacac aataaattgt attactaata caagcattag ttatgcatac gttagaaaag    180
tgtactaaac aaggtactag t                                              201
```

<210> SEQ ID NO 19
<211> LENGTH: 201
<212> TYPE: DNA
<213> ORGANISM: Solanum lycopersicum

<400> SEQUENCE: 19

```
gcatgcattt agaagagaaa tgctgtttta taaacttcaa ctaaaataac ctgcaatttc    60
tttaaacatt gaagaaaggc catgagcaac attgctaggg atgggttggg caccctcatc    120
accaaggacc aatttagcat ctgcattcat caccgcaaca tcaaacatgg gacgtaatcc    180
cacgtagtgt tgcatggcac t                                              201
```

<210> SEQ ID NO 20
<211> LENGTH: 101
<212> TYPE: DNA
<213> ORGANISM: Solanum lycopersicum

<400> SEQUENCE: 20

```
aaatttcctc ttttctacct caaattcgta cagcaagagc atgcttggca tgagaccaaa    60
cacacgcgga gattccggag gtaaccatgg tatggtcatg t                        101
```

<210> SEQ ID NO 21
<211> LENGTH: 201
<212> TYPE: DNA
<213> ORGANISM: Solanum lycopersicum

<400> SEQUENCE: 21

```
cacatattaa tgaaaggaat atcccaattc aaattgatgt caccatagga ccatcaacta    60
gtggcatagc taatgagtca aaagcacgcc taaagcgtgg caggccattt ggatcaaaac    120
cctagaaaat gaaaatcaaa agatcaaaat gacactatga aaaaacctca catagaaagt    180
caagacgtga gtaattctga t                                              201
```

<210> SEQ ID NO 22
<211> LENGTH: 201
<212> TYPE: DNA
<213> ORGANISM: Solanum lycopersicum

<400> SEQUENCE: 22

```
tcaatcaata ggagcgacgg gcggtgtgta caaagggtag ggacgtagtc aatgcgagct    60
gatgactcgt gcttactagg aattccttgt tgaaaaccaa caaatgcaat gatatatccc    120
tatcacgatg aaatttcaaa gattacccgg gcctattggc caaggctata aactcgttga    180
ataatcagtg tagcgcgcgt g                                              201
```

<210> SEQ ID NO 23
<211> LENGTH: 201
<212> TYPE: DNA
<213> ORGANISM: Solanum lycopersicum

<400> SEQUENCE: 23

```
ttcaataagc ttaatactta atggatctaa gaatatatat tattcatttg atcaatttga    60
gataaactat aaaccataca ataataatct atacataaat aaagagtcta taacaatcta    120
tacatgaatt cattaatatc aaagcatgat cacacaaccc atatttaagt caaattgaga    180
```

```
gatttgagaa ggtcaagggt t                                              201

<210> SEQ ID NO 24
<211> LENGTH: 201
<212> TYPE: DNA
<213> ORGANISM: Solanum lycopersicum

<400> SEQUENCE: 24
ggaggtgtct ggccctgatc agataacccg ctaagataag ccagaacctg attgatcatc    60
tctggggtag gttggggtgg catttcctca ttctacactt tttcattctc ctcatcctcc   120
ccttctctta ctacttcctc agttggtgga ggagtcaccg ccctagtacc agatgggcca   180
ggcgttcgtc ctcttcctct a                                              201

<210> SEQ ID NO 25
<211> LENGTH: 201
<212> TYPE: DNA
<213> ORGANISM: Solanum lycopersicum

<400> SEQUENCE: 25
ggaccttcca cataagtttc aacaaaaacg aacacgtaaa acatgtaaag gtacaccaag    60
acacacatgc atgtctcaag tctaaccttc aaacgtcatc agacattctt ggacatttga   120
cctccaaatg atttcaaatt aatcatacat tcttaaaaca cttaattaac aggtgaacaa   180
gattattaca cacatgtgag g                                              201

<210> SEQ ID NO 26
<211> LENGTH: 201
<212> TYPE: DNA
<213> ORGANISM: Solanum lycopersicum

<400> SEQUENCE: 26
gttgaaggtt ccacataaag gaccttatta gaaacattca aggtctcatg tcattcgtac    60
atacaagact aagagacttt agcatcctaa ttcaatacat atgatattca tattcatcca   120
tgtatcaagt aagggacaca agtctaccac acaagataca caaatacttc actttacccc   180
atataacata taattctaga a                                              201

<210> SEQ ID NO 27
<211> LENGTH: 201
<212> TYPE: DNA
<213> ORGANISM: Solanum lycopersicum

<400> SEQUENCE: 27
aaccaacatt ayacaattca tatcaagata acaacctrgg gttaagtgtt aaaggtcatt    60
ttctacaaac tagactgatt tatcaacaaa taacataatt aagttaaagt acatgttaaa   120
ctattcatga catccataat aaatcataaa taaagtaatt cacaagccca atttcaagat   180
ttgaaaagac tcacttgaat t                                              201

<210> SEQ ID NO 28
<211> LENGTH: 201
<212> TYPE: DNA
<213> ORGANISM: Solanum lycopersicum

<400> SEQUENCE: 28
cgctaaagga accgaataaa atgggagatc ttcggagaga atggattttg ttgaagttgg    60
ggaagtgtgg aatcttgtga tggaatgaga gtgaatgggt taggtagtgg ggggaaaaaa   120
```

```
gaggaaatag ggagggaaac ggttaagggg gttatgtaaa gaggtgggta actgaagagt      180
ttaaaaactt ttcatatgta g                                                201

<210> SEQ ID NO 29
<211> LENGTH: 201
<212> TYPE: DNA
<213> ORGANISM: Solanum lycopersicum

<400> SEQUENCE: 29
aactctcata ctcgttcatt caatgtcctg attttgttg gcctgtatcg tatcatgatg       60
catacgcagg taacgaggat cgacatccaa tgcatcattg gttcagttga gcactccaga      120
gtcggttggt gcgcctcttt gcttttgga ggatccattt tatttctttc tagtttagtt      180
tattaggatc tgtcccaaca c                                                201

<210> SEQ ID NO 30
<211> LENGTH: 201
<212> TYPE: DNA
<213> ORGANISM: Solanum lycopersicum

<400> SEQUENCE: 30
gatttaatga acaagatatt caaacaatat ttggacttgt ttgtcattgt ctttatttat      60
aatatcccga tttattctca aagtgagaaa gagcatccga accatatgag agtttctatg      120
caaactctca aagatcgaca attattcact aagttcaaca aatgttaatt cttgttacag      180
tcggttgcat tccttggtca t                                                201

<210> SEQ ID NO 31
<211> LENGTH: 201
<212> TYPE: DNA
<213> ORGANISM: Solanum lycopersicum

<400> SEQUENCE: 31
agaaacaact aaattaagtt gttgccattt gacaatataa gccaacaata atttcgttgt      60
tgctaaaacg ttgctgcgaa ttgtacattt tcttgtagtg tgtgacagaa attgttgctt      120
gtcttagcaa ggtttacgat gatcatctca gcaggttagt tttacatagc atccactaat      180
ttgytggaat tttctgaaaa a                                                201

<210> SEQ ID NO 32
<211> LENGTH: 201
<212> TYPE: DNA
<213> ORGANISM: Solanum lycopersicum

<400> SEQUENCE: 32
ttttaaattg gttccatttt ttactataaa attctttttg aatttgtttt cgtgccaggg      60
atcctggact aaaatcaatg agtcgattaa acataattaa gcatcattga gatcagttga      120
tttatcaaca ctgaagtcca tttctgactg agttggatcc atatctgaca acttatcagt      180
tgcttgaaca atatttgttc t                                                201

<210> SEQ ID NO 33
<211> LENGTH: 201
<212> TYPE: DNA
<213> ORGANISM: Solanum lycopersicum

<400> SEQUENCE: 33
gatggattcg taaattcaat acgtgattcc aagataagca tgttaatttt aggaaaaaaa      60
tcttcaattt tcttttacca ttttctttc tttgggtgga agattcctc gtcttcaaat       120
```

```
ggaaatacta aacgaaatgt tactttgaca aaagaacgtt ccttctcttt tggaggaatg    180
acttcattat gatagtggac t                                              201

<210> SEQ ID NO 34
<211> LENGTH: 201
<212> TYPE: DNA
<213> ORGANISM: Solanum lycopersicum

<400> SEQUENCE: 34
tgttactctt atatgaagtt gtttacgtta atgaacatgt tattggtctt acttctttat    60
gaggtgataa gtacttatgt tacaagttat atgaagcaaa cctttactta tggtctccta    120
tcttatttat tttgttgtgt aacacctaaa tatgaactat ggtgaacttg agcttcgtaa    180
gtgtttcttt aattatatga a                                              201

<210> SEQ ID NO 35
<211> LENGTH: 201
<212> TYPE: DNA
<213> ORGANISM: Solanum lycopersicum

<400> SEQUENCE: 35
tggtaatgga ataatagtt acaatcacgg aaagtcacat atttactgtg agttctacca     60
ttacaaaggt cacactaaag agacttacaa gctttatgac catcctaaga agaaagatgg    120
agcatcgatc tatccctcat gttaaggttg tttctattgg ggaatcaact cactaaggct    180
agagttatga ctaggtccta t                                              201

<210> SEQ ID NO 36
<211> LENGTH: 201
<212> TYPE: DNA
<213> ORGANISM: Solanum lycopersicum

<400> SEQUENCE: 36
tttgcacatg gccaagatat actagaaacg cattatagtt ttgttaaatg ttttatccta    60
agttttggct rtaaggtaaa ctattactca agcatggagc ctgtcttaat aatatacata    120
ttaatgtata gcagttctaa cataggtttc aggctgcccc tttcttcaac aattaacggg    180
gacttacaat accacatgct c                                              201

<210> SEQ ID NO 37
<211> LENGTH: 201
<212> TYPE: DNA
<213> ORGANISM: Solanum lycopersicum

<400> SEQUENCE: 37
ttatccttcc cttggatttt gagaaagccg caaattctta atttctccca ttcgagttga    60
ctcgtagaaa aggcgaaaag gtcccgaagt ttaaagaatc aaagaagatt gaagaaattg    120
aatggtttgg gcaaaaagtc caaaaatttt attttggaaa atgttgtat tttatttggg     180 cctaagccct tttgtattgt t                                              201

<210> SEQ ID NO 38
<211> LENGTH: 201
<212> TYPE: DNA
<213> ORGANISM: Solanum lycopersicum

<400> SEQUENCE: 38
ccagatcgtg cttagattga ttttgaact ccatttcagc agattcagtg gtgagtcctc     60
```

| | |
|---|---:|
| atcctctaag gacgatattc atgagtttct ttttagtgtt tggttctttt gtttcagttt | 120 |
| ttgctagact tttttggggc ttatgccaac atttctagtc agtttagagg ctattttcag | 180 |
| acatagttag tttcagctta g | 201 |

<210> SEQ ID NO 39
<211> LENGTH: 201
<212> TYPE: DNA
<213> ORGANISM: Solanum lycopersicum

<400> SEQUENCE: 39

| | |
|---|---:|
| acaccgatgc aactttgctt tcattttgat atatgtcaca ctagaaacag tgctacattt | 60 |
| taaatattta aatgtagtgg gagtattata tctatgtaaa ttttttatg ctattttttg | 120 |
| ggtttcatgg aagtttttt tcgatactt ggccaaggac agtcccgttt aactatataa | 180 |
| tttttaaat tttctaggat t | 201 |

<210> SEQ ID NO 40
<211> LENGTH: 201
<212> TYPE: DNA
<213> ORGANISM: Solanum lycopersicum

<400> SEQUENCE: 40

| | |
|---|---:|
| gtccctccaa ggcttcgctt gcttaaataa tagggaaata tacatctttt tggctgatcg | 60 |
| ctaagtatac ttggcgatgc ttaggtgttt ctcttcatat cttttcatca tttttttcacg | 120 |
| ttttgcgcct aagtgtcact gccaacacta aaacttcaaa tacttgaaac ttaagagttt | 180 |
| tcatcagaca ttgagataga a | 201 |

<210> SEQ ID NO 41
<211> LENGTH: 201
<212> TYPE: DNA
<213> ORGANISM: Solanum lycopersicum

<400> SEQUENCE: 41

| | |
|---|---:|
| aacattaaaa tatgtgtata cgatgaatat atgatgtttt catgaggttt ccttgatgaa | 60 |
| ttttactagt tgattatgaa ggtgatcatt gtgatttagg ccgttaaagg tgtgatttag | 120 |
| gctattaatt ctattgtctt gttttagtgt tctagattga tcttttttaat tcaattgtct | 180 |
| tgaaattaat tgatcgtagt a | 201 |

<210> SEQ ID NO 42
<211> LENGTH: 201
<212> TYPE: DNA
<213> ORGANISM: Solanum lycopersicum

<400> SEQUENCE: 42

| | |
|---|---:|
| gtgtccaagg caaacctaca acaaaatcca cattgatgtc ttcccacatc caagtaggaa | 60 |
| cttggatttc ttggagtaaa ccacctgact tttggtgttc agcttttact tcttggcaat | 120 |
| ttggagattt tgcaacaaat tccactatat ccttcttcaa gccttcccac caaaacactt | 180 |
| cgctaaggtc atggttcatc t | 201 |

<210> SEQ ID NO 43
<211> LENGTH: 201
<212> TYPE: DNA
<213> ORGANISM: Solanum lycopersicum

<400> SEQUENCE: 43

| | |
|---|---:|
| tctcctatgg cctatacaga tatatgatgg ttaatgaagg cttaaagaca ttttaaaaag | 60 |

```
ggactttatc ttagcaccga gcgaactaaa tatgagaggt gttttttccc aatgtgggaa        120
ggtaggtttg taatggttct tatgagatgg agataacagt gcaatgttca taaagacggt        180
ctctagcata tatcctagtt a                                                  201
```

<210> SEQ ID NO 44
<211> LENGTH: 201
<212> TYPE: DNA
<213> ORGANISM: Solanum lycopersicum

<400> SEQUENCE: 44

```
tccatctttg aacatagtag tatttttct ttagacttca tgttgttggg atatgtatga         60
aataatgttg ttcacattcc caatatttcc cgcatcaacc gaaaaattgt taattttttac       120 gagctcttct cacctagatt tctctatatt aatcgattgg atgaatttgc tgatattaga        180
gtaaaccgat aacctacatc c                                                  201
```

<210> SEQ ID NO 45
<211> LENGTH: 201
<212> TYPE: DNA
<213> ORGANISM: Solanum lycopersicum

<400> SEQUENCE: 45

```
gtttgattag ttgtttgttt ataatttttcg ttttgggttc ttcaagtgtg aagaacttta       60
gtttacctac tgttattgta cgttatttgg cagagaaaaa cgtgagtgag agtaatagag        120
acgtgagaga gagagatgag catgggagag aagagttttc ttaggcttag gagtctagtt        180
taggacttag tcaaataagt t                                                  201
```

<210> SEQ ID NO 46
<211> LENGTH: 201
<212> TYPE: DNA
<213> ORGANISM: Solanum lycopersicum

<400> SEQUENCE: 46

```
atctgcaaac aaaaagtgac aacattaata ggaggatmca ttagccaagt kttgtgtgct        60
ttggaaaatc gacattgact aatggtacag aacatcaacc awcctaaaca catgtaacat       120
gccatgtgcg catcttgaaa acaactttga ccaatggaac gcaacatwag aaaaggccgg       180
tccactttgt gcaagaggca t                                                  201
```

<210> SEQ ID NO 47
<211> LENGTH: 201
<212> TYPE: DNA
<213> ORGANISM: Solanum lycopersicum

<400> SEQUENCE: 47

```
gtttaggtta gcgtgtagtg gtatttttta gggtgtgggg ttaaggattt gaagttaaat        60
atctatggtg tagtgtttaa ttttttggat tttgtatttt tgtcatgagg tttagggtat       120
agggtatagg ttaaagtgtt atgattaggg ttagggctaa ggttagaggt agggttawga       180
tttagtgttc gagtttagga t                                                  201
```

<210> SEQ ID NO 48
<211> LENGTH: 201
<212> TYPE: DNA
<213> ORGANISM: Solanum lycopersicum

<400> SEQUENCE: 48

```
aatgttgtca tgtttgcttt aaaaatttat atataaaaat ataaaagtat tttatacaaa      60
atatatagaa aaaattgagg agaaaaaaac ttgattttttt taaaaaaatt ggaccaattg    120
gtgaaaaaaa attggctcta aaaactaaac tctaaaattt aaatagtcat ccaaatatat    180 ttatatttt aaaatctaac a                                               201

<210> SEQ ID NO 49
<211> LENGTH: 201
<212> TYPE: DNA
<213> ORGANISM: Solanum lycopersicum

<400> SEQUENCE: 49
tagaagatga tggactttct gatgtatctg agctgctatt ctcactttgt ctatctttat    60
ttgaccatag ttttgggaac atcttttttgg accaattatt aaagattgat aaacttggat   120
agtggtagat ttgatctct agcaacttca gtatcgatta ccttagccac ctttactccg    180
gaatcatctg atgcaaacgg g                                              201

<210> SEQ ID NO 50
<211> LENGTH: 201
<212> TYPE: DNA
<213> ORGANISM: Solanum lycopersicum

<400> SEQUENCE: 50
atatcataac atttaagagt acataacatc atgatacttt aacaatatag accaacacat    60
attcataagt gacacaatca acatatagta tcaacaatgt tcaagtttat catatgcatg    120
ccagataaca ttacaatcat attcatacat aagaacatcc tcctaagact cccttcaagg    180
ctaactagtg cgatgttttg t                                              201

<210> SEQ ID NO 51
<211> LENGTH: 201
<212> TYPE: DNA
<213> ORGANISM: Solanum lycopersicum

<400> SEQUENCE: 51
ctctcacttt gaatattcag tttcctcatt tcatcaatag gaagtgttcc ttcccctata    60
tttccctgat aattgctcaa attagctcca acacaccac catttctact agctccaaaa    120 acaaacccttt cattaccaac atccccacta ccctatcaa cccagaagc aaaacccaca    180 ttcccaaatt tcccaggaac c                                              201

<210> SEQ ID NO 52
<211> LENGTH: 111
<212> TYPE: DNA
<213> ORGANISM: Solanum lycopersicum

<400> SEQUENCE: 52
ggtattcact atcctgtatt aatatctgtt gcacatgttc cagaacttaa ctatataaga    60
gttgaggatg atggcttaga aataggtgct ggagttaagt tgtcacagct t             111

<210> SEQ ID NO 53
<211> LENGTH: 201
<212> TYPE: DNA
<213> ORGANISM: Solanum lycopersicum

<400> SEQUENCE: 53
taaagtagcg tgtaaccatt ggtgatgcat gtaaagggaa ttttctaaat acaatcattt    60
tttcttcaaa gttaaccatt tgtagcttta actgttcaat agccttgcac ataaggtgta   120
```

```
tccttcttgg ccctctgttt agacaaagta ccatcaatag gatgagagtt acagaaaaaa        180
gtagcagaag tacttctcag a                                                  201
```